(12) United States Patent
Pelzer et al.

(10) Patent No.: US 6,566,110 B1
(45) Date of Patent: May 20, 2003

(54) NUCLEIC ACID FRAGMENT AND VECTOR COMPRISING A HALOGENASE, AND A PROCESS FOR HALOGENATING CHEMICAL COMPOUNDS

(75) Inventors: Stefan Pelzer, Moessingen (DE); Petra Huber, Sachsenheim (DE); Roderich Suessmuth, Tuebingen (DE); Juergen Recktenwald, Poltringen (DE); Dorothee Heckmann, Schwalbach/Elm (DE); Wolfgang Wohlleben, Tuebingen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/429,610

(22) Filed: Oct. 29, 1999

(30) Foreign Application Priority Data

Jun. 11, 1999 (DE) .......................... 199 26 770

(51) Int. Cl.[7] .............................. C12N 9/14; C12N 1/20; C12N 15/00; C12P 9/00; C07H 21/04

(52) U.S. Cl. .................... 435/195; 435/131; 435/252.3; 435/320.1; 435/440; 536/23.2

(58) Field of Search ................................ 435/195, 131, 435/252.3, 320.1; 536/23.2

(56) References Cited

U.S. PATENT DOCUMENTS

| | | | |
|---|---|---|---|
| 4,326,031 A | 4/1982 | Wandrey et al. | 435/146 |
| 4,782,020 A | 11/1988 | Leuchtenberger et al. | 435/106 |
| 4,923,811 A | 5/1990 | Simon et al. | 435/136 |
| 5,427,924 A * | 6/1995 | Arthur et al. | 435/69.5 |

FOREIGN PATENT DOCUMENTS

| | | |
|---|---|---|
| DE | 29 30 087 | 2/1981 |
| DE | 33 07 094 | 9/1984 |
| DE | 36 31 228 | 3/1988 |
| DE | 42 26 102 | 2/1994 |
| EP | 0 023 346 | 2/1981 |
| EP | 249 676 | 12/1987 |
| EP | 0 335 528 | 10/1989 |
| EP | 388 186 | 9/1990 |
| EP | 0 468 504 | 1/1992 |
| EP | 0 521 408 | 1/1993 |
| WO | WO 93/21334 | 10/1993 |

OTHER PUBLICATIONS

GenEmbl database—Accession # U84350, 1997.*
GenEmbl database—Accession # U84349, 1997.*
Wageningen et al. Sequencing and analysis of genes involved in the biosynthesis of a vancomycin group antibiotic. Chem. Biol. 3, 155–162 (1998).*
Pelzer et al. Identification and analysis of the balimycin biosynthetic gene cluster and tis use for manipulating glycopeptide biosynthesis in Amycolatopsis mediterranei DSM5908. Antimicrob. Agents Chemother. 43 (7), 1565–1573 (1999).*
Kren et al. "Biotransformation of Ergot Alkaloids by Haloperoxidase from *Streptomyces aureofaciens:* Stereoselective Acetoxylation and Propionoxylation" Leibigs Ann. Recueil (1997) pp. 2379–2383.
De Schrliver et al. "Thiocarbamate Herbicide–Inducible Noheme Haloperoxidase of *Rhodococcus erythropolis* N186/21" Applied and Environmental Microbiology vol. 63. No. 5, (1997) pp. 1911–1916.
vanWageningen "Sequencing and Analysis of Genes Involved in the Biosynthesis of a Vancomycin Group Antibiotic" Chemistry & Biology (1998) pp. 155–162.
Hohaus et al. "NADH–Dependent Halogenases Are More Likely to Be Involved in Halometabolite Biosynthesis Than Haloperoxidases" Angew. Chem. Int. Ed. vol. 36 No. 18 (1997) pp. 2012–2013.
Heinz van Pee' "Biosynthesis of Halogenated Metabolites by Bacteria" Annu. Rev. Microbio. (1996) pp. 375–399.
Kirner et al. "Functions Encoded by Pyrrolnitrin Biosynthetic Genes from *Pseudomonas Fluorescens*" J. Bacteriology (1998) pp. 1939–1943.
Hammer et al. "Four Genes fro m*Pseudomonas fluorescens* That Encode the Biosynthesis of Pyrrolnitrin" Applied and Environmental Microbiology vol. 63 (1997) pp. 2147–2154.
Nowak–Thompson et al. "Characterization of the Pyoluteorin Biosynthetic Gene Cluster of *Pseudonomas fluorescens* Pf–5" Journal of Bacteriology vol. 181 (1999) pp. 2166–2174.
Solenberg et al. "Production of Hybrid Glycopeptide Antiboitics in vitro and in *Streptomyces toyocaensis*" Chemistry & Biology vol. 4, (1997) pp. 195–202.
Dairi et al. "Cloning and Nucleotide Sequence of the Gene Responsible for Chlorination of Tetracyclin" Biosci. Biotech, Biochem. vol. 59 (1995) pp. 1099–1106.

(List continued on next page.)

Primary Examiner—Ponnathapu Achutamurthy
Assistant Examiner—Yong Pak
(74) Attorney, Agent, or Firm—Keil & Weinkauf

(57) ABSTRACT

The invention relates to a process halogenation, which comprises halogenating a chemical compound in the presence of a halogenase, where the halogenase is (a) encoded by the sequence specified in SEQ ID NO: 1 or a sequence derived therefrom on the basis of the degeneracy of the genetic code, or is (b) encoded by a nucleic acid sequence which codes for a functional fragment of (a) or (c) by a sequence which hybridizes with (a) or (b) under standard conditions, or is (d) encoded by a sequence which has more than 30% identity or more than 60% similarity with the sequence specified under (a).

5 Claims, No Drawings

OTHER PUBLICATIONS

Pelzer et al. "Cloning and analysis of a peptide shythetase gene of the balhimycin producer *Amycolatopsis mediterranei* DSM5908 and development of a gene disruption/replacement system" J. of Biotechnology vol. 56 (1997) pp. 115–128.

Potrykus "Gene Transfer to Plants: Assessment of Published Approaches and Results" Annu. Rev. Plant Physical Plant Mol. Biol. vol. 42 (1991) pp. 205–225.

Bevan "Binary Agrobacterium vectors for plant transformation" Nucleic Acid Research vol. 2 No. 22 (1984) pp. 8711–8721.

Höfgen et al. "Storage of Competent Cells for Agrobacterium Transformation" Nucleic Acid Research vol. 16, No. 20 (1988) pp. 9877.

Wohlleen et al. "Streptomyces plasmid vectors" Plasimds: A Practical Approach (1993) pp. 147–175.

Hillamenn et al. "Gene Disruption and gene replacement in Strptomyces via single stranded DNA transformation on integration vectors" Nucleic Acids Research vol. 19 No. 4 (1991) pp. 727–731.

Oh et al. "Denaturation of Circular or Linera DNA Facilities Targeted Integrative Transformation of *Strptomyces coelicolor* (A3(2): Possible Relevance to Other Organisms" Jnl. of Bacteriology vol. 179 No. 1 (1997) pp. 122–127.

Baltz et al. "Genetic Manipulation of antibiotic–producing Streptomyces" Trends in Microbiology vol. 6, No. 2, (1988) pp. 76–83.

Flett et al. "High efficiency intergeneric conjugal transfer of plasmid DNA of *Escherichia coli* to methyl DNA–restricting steptomycetes" FEMS Microbiology Letter vol. 155 (1997) pp. 223–229.

English et al. "Transformation of *Saccharopolyspora erythraea* by electroporation of germinating spores: construction of propionly Co–A carboxylate mutants" Jnl. of Industrial Micribiology & Biotechnology vol. 21 (1998) pp. 219–224.

Lal et al. "Construction of a Hybrid Plasmid Capable of Replication in *Amycolatopsis mediterranei*" Applied and Environmental Microbiology vol. 57, No. 3, (1991) pp. 665–671.

Madon et al. "Transformation System for *Amycolatopsis (Nocardia) mediterranei*: Direct Transformation of Mycelium with Plasmid DNA" Jnl of Bacteriology vol. 173, No. 20 (1991) pp. 6325–6331.

Vrijbloed et al. "Transformation of the Methylotrophic Actinomycete *Amycolatopis methanolica* with Plasmid DNA: Stimulatory Effect of a pMEA300–Encoded Gene" Plasmid vol. 34 (1995) pp. 96–104.

Kumar et al. "Efficient Transformation of the Cephamycin C Producer *Nocardia lactamdurans* and Development of Shuttle and Promoter–Probe Cloning Vectors" Applied and Environmental Microbiology vol. 60, No. 11 (1994) pp. 4086–4093.

Greasham et al. "Design and optimization of growth media" Applied Microbiology Physiology, A Practical Approach (1997) pp. 53–74.

Nadkarni et al. "balhimycin, A New Glycopeptide Antibiotic Produced by Amycolatopsis sp. Y–86.21022 Taxonomy, Production, Isolation and Biological Activity" The Journal of Antibiotics (1994) pp. 334–341.

Franck et al. "Nucleotide Sequence of Cauliflower Mosaic Virus DNA" Cell vol. 21, (1980) pp. 285–294.

Ward et al. "Chemical Regulation of Transgene Expression in Plants" Plant Molecular Biology vol. 22 (1993) pp. 361–366.

Gatz et al. "Stringent Repression and Homogeneous De–repression by tetracyclin of a modified CaMV 35S promoter in intact transgenic tobacco plants" The Plant Journal vol. 2 No. 3 (1992) pp. 397–404.

Stockhaus et al. "Correlation of the Expression of the Nuclear Photosynthetic Gene ST–LS1 with the Presence of Chloroplasts" The EMBO Journal vol. 8, No. 9 (1989) pp. 2445–2451.

Glick et al. "Method in Plant Molecular Biology" pp. 71–119.

Spee et al. "Efficient random mutagenesis method with adjustable mutation frequency by us of PCR and dITP" Nucleic Acids Research vol. 21 No. 3 (1993) pp. 777–778.

Stemmer et al. "DNA Shuffling by random fragmentation and reassembly: In vitro recombinant for molecular evolution" Porc. Natl. Acad. Sci. vol. 91 (1994) pp. 10747–10751.

Steiner et al. "Homologous recombination as the Main Mechanism for DNA Integration and Cause of Rearrangements in the Filamentous Ascomycete *Ashbya gossypii*" Genetics vol. 140 (1995) pp. 972–987.

Matsushima et al. "Efficient Transformation of *Amycolatopsis orientalis* (*Nocardia orientalis*) Protoplasts by Strptomyces Plasmids" Jnl. Bacteriology vol. 169, No. 5 (1987) pp. 2298–2300.

Dao et al. Developmental cheating and the evolutionary biology of Dictyostelium and Myxococcus Microbiology vol. 146 (2000) pp. 1505–1512.

Murakami et al. "Thiostrepton–Induced Gene Expression in *Streptomyces lividans* " Jnl. of Bacteriology (1989) pp. 1459–1466.

Takano et al. "Construction of thiostrepton–inducible, high–copy–number expression vectors for use in Streptomyces spp." Gene vol. 166 (1995) pp. 133–137.

Moretti et al. "Isolation and Characterization of an Extrachromosomal Element from *Nocardia mediterranei*" Plasmid vol. 14 (1985) pp. 126–133.

Schmitt et al. "Promote constructions for efficient secretion expression in *Streptomyces lividans*" Appl. Microbiol. Biotechnol. vol. 36 (1992) pp. 493–498.

Bugeja et al. "Differentation of *Saccharomyces cerevisiae* at Slow Growth Rate in Glucose–limited Chemostat Culture" Jnl. General Microbiology vol. 128 (1982) pp. 2707–2714.

Bibb et al. "Unusual Features of Transcription and Translation of Antibiotic Resistance Genes in Antibiotic–Producing Strewptomyces" 5th Intl. Symp. on Genetics of Industrial Microorganisms (1996) pp. 309–319.

Quiros et al. "Two glycosyltransferases and a glycodase are involved in oleandomycin modification during its biosynthesis by *Streptomyces antibioticus*" Molucular Microbiology vol. 26 No. 6 (1998) pp. 1177–1185.

Gaisser et al. Cloning of an Avilamycin Biosynthetic Gene Cluster from *Streptomyces viridochromogenes* Tü 57 Jn. Bacteriology vol. 179 No. 20 (1997) pp. 6217–6278.

Pelzer et al. "Identification and Analysis of the Balhimycin Biosynthetic Gene Cluster and Its Use for Manipulating Glycopeptide Biosynthesis in *Amycolatopsis mediterranei* DSM5908" Antimocrobial Agents and Chemotherapy vol. 43 No. 7 (1999) pp. 1565–1573.

Pelzer et al. "Cloning and analysis of a peptide synthetase gene of the balimycin producer *Amycolatopsis mediterranei* DSM5908 and development of a gene disruption/replacement system" Jnl. of Biotechnology vol. 56 (1997) pp. 115–128.

Sanger et al. "DNA Sequencing with chain–terminating inhibitors" Proc. Natl. Acad. Sci. vol. 74, No. 12 (1977) pp. 5463–5467.

Staden et al. "Codon Preferences and its Use in Identifying Protein Coding Regions in Long DNA Sequences" Nucleic Acid Research vol. 10, No. 1 (1982) pp. 141–156.

Pelzer et al. "Database EMBL Sequence [Online]" XP002146262 (1998) pp. 1–7.

Van Wageningen et al. "Database EMBL Sequence [Online]" XP002146263 (1997) pp. 1–19.

Van Wageningen et al. "Database BIOSIS Sequence [Online]" XP002146270 (1998) p. 1.

Solenberg et al. "Database BIOSIS [Online]" XP002146271 (1997) p. 1.

* cited by examiner

SEQUENCE LISTING

<160> NUMBER OF SEQ ID NOS: 2

<210> SEQ ID NO 1
<211> LENGTH: 1620
<212> TYPE: DNA
<213> ORGANISM: Amycolaptosis mediterranei
<220> FEATURE:
<221> NAME/KEY: CDS
<222> LOCATION: 84 ... 1559

<400> SEQUENCE: 1

```
atcgggttcc ggtcacctgg tagcgcaatc cgggttgaaa accagcctcg gcaatttgac      60
actcgacaga ggaatggtgg ag atg tcg gtc gaa gac ttc gac gtg gtg gtg     113
                         Met Ser Val Glu Asp Phe Asp Val Val Val
                           1               5                  10 gcg ggc ggc ggg ccg ggt ggt tcg acg gtg gcc acg ctg gtg gcc atg      161
Ala Gly Gly Gly Pro Gly Gly Ser Thr Val Ala Thr Leu Val Ala Met
             15                  20                  25 cag gga cac cgg gtg ctg ctg ctg gag aaa gag gtt ttc ccg cgg tat      209
Gln Gly His Arg Val Leu Leu Leu Glu Lys Glu Val Phe Pro Arg Tyr
         30                  35                  40 cag atc ggt gag tcg ctg ctg ccc gcc acg gtg cac ggc gtg tgc cgg      257
Gln Ile Gly Glu Ser Leu Leu Pro Ala Thr Val His Gly Val Cys Arg
     45                  50                  55 atg ctc ggc atc tcc gac gag ctg gcc aat gcc ggg ttc ccg atc aag      305
Met Leu Gly Ile Ser Asp Glu Leu Ala Asn Ala Gly Phe Pro Ile Lys
 60                  65                  70 cgc ggc ggc acg ttc cgc tgg ggc gcc cgg ccg gag ccg tgg acg ttc      353
Arg Gly Gly Thr Phe Arg Trp Gly Ala Arg Pro Glu Pro Trp Thr Phe
75                  80                  85                  90 cac ttc ggc atc tcg gcc aag atg gcc ggc tcg acg tcg cac gcc tac      401
His Phe Gly Ile Ser Ala Lys Met Ala Gly Ser Thr Ser His Ala Tyr
                 95                 100                 105 cag gtc gag cgg gcg cgg ttc gac gag atg ctg ctg aac aac gcc aag      449
Gln Val Glu Arg Ala Arg Phe Asp Glu Met Leu Leu Asn Asn Ala Lys
            110                 115                 120 cgc aag ggc gtg gtc gtg cgg gag ggg tgc gcg gtc acc gat gtg gtg      497
Arg Lys Gly Val Val Val Arg Glu Gly Cys Ala Val Thr Asp Val Val
        125                 130                 135 gaa gac ggc gag cgg gtc acc ggt gcg cgg tac acc gat ccc gac ggc      545
Glu Asp Gly Glu Arg Val Thr Gly Ala Arg Tyr Thr Asp Pro Asp Gly
    140                 145                 150 acc gag cgg gaa gtg tcg gcg cgg ttc gtg atc gac gcg tcg ggc aac      593
Thr Glu Arg Glu Val Ser Ala Arg Phe Val Ile Asp Ala Ser Gly Asn
155                 160                 165                 170 aag agc cgg ctc tac acc aag gtc ggc ggt tcg cgg aac tat tcg gag      641
Lys Ser Arg Leu Tyr Thr Lys Val Gly Gly Ser Arg Asn Tyr Ser Glu
                175                 180                 185 ttc ttc cgc agc ctc gcg ctg ttc ggt tac ttc gag ggt ggc aag cgg      689
Phe Phe Arg Ser Leu Ala Leu Phe Gly Tyr Phe Glu Gly Gly Lys Arg
            190                 195                 200 ctg ccc gag ccg gtc tcc ggg aac atc ctg agt gtg gcc ttc gac agc      737
Leu Pro Glu Pro Val Ser Gly Asn Ile Leu Ser Val Ala Phe Asp Ser
        205                 210                 215 ggc tgg ttc tgg tac atc ccg ctg agc gac acg ctg acc agc gtc ggc      785
Gly Trp Phe Trp Tyr Ile Pro Leu Ser Asp Thr Leu Thr Ser Val Gly
    220                 225                 230 gcg gtg gtg cgc cgg gag gac gcc gag aag atc cag ggt gac cgg gag      833
Ala Val Val Arg Arg Glu Asp Ala Glu Lys Ile Gln Gly Asp Arg Glu
```

```
                235                 240                 245                 250
aag gcc ctc aac acg ctg atc gcc gag tgc ccg ctg atc tcg gaa tac         881
Lys Ala Leu Asn Thr Leu Ile Ala Glu Cys Pro Leu Ile Ser Glu Tyr
                        255                 260                 265 ctc gcg gac gcg acc cgg gtg acg acc ggc cgg tac ggg gaa ctg cgc         929
Leu Ala Asp Ala Thr Arg Val Thr Thr Gly Arg Tyr Gly Glu Leu Arg
                270                 275                 280 gtc cgc aag gac tac tcc tac cag cag gag acc tac tgg cgg ccg ggc         977
Val Arg Lys Asp Tyr Ser Tyr Gln Gln Glu Thr Tyr Trp Arg Pro Gly
            285                 290                 295 atg atc ctg gtc ggc gac gcc gcg tgt ttc gtg gac ccg gtg ttc tcc        1025
Met Ile Leu Val Gly Asp Ala Ala Cys Phe Val Asp Pro Val Phe Ser
        300                 305                 310 tcc ggt gtg cac ctg gcg acc tac agc gcg ctg ctc gcg gcc cgg tcg        1073
Ser Gly Val His Leu Ala Thr Tyr Ser Ala Leu Leu Ala Ala Arg Ser
315                 320                 325                 330 atc aac agc gtc ctc gcc ggc gac ctg gac gag aag acc gcg ctg aac        1121
Ile Asn Ser Val Leu Ala Gly Asp Leu Asp Glu Lys Thr Ala Leu Asn
                335                 340                 345 gag ttc gag ctg cgg tat cgc cgt gag tac ggc gtg ttc tac gag ttc        1169
Glu Phe Glu Leu Arg Tyr Arg Arg Glu Tyr Gly Val Phe Tyr Glu Phe
            350                 355                 360 ctc gtg tcc ttc tac cag atg aac gtg aac gag gag tcg tac ttc tgg        1217
Leu Val Ser Phe Tyr Gln Met Asn Val Asn Glu Glu Ser Tyr Phe Trp
        365                 370                 375 cag gcc aag aag gtc acg cag aac cag agc acc gac gtc gag tcg ttc        1265
Gln Ala Lys Lys Val Thr Gln Asn Gln Ser Thr Asp Val Glu Ser Phe
    380                 385                 390 gtc gag ctg atc ggc gga gtg tcg tcc ggg gag acc gcg ctg acg gcc        1313
Val Glu Leu Ile Gly Gly Val Ser Ser Gly Glu Thr Ala Leu Thr Ala
395                 400                 405                 410 gcc gac cgc atc gcc gcg cgc agt gcc gag ttc gcc gcg gcg gtg gac        1361
Ala Asp Arg Ile Ala Ala Arg Ser Ala Glu Phe Ala Ala Ala Val Asp
                415                 420                 425 gag atg gcg ggc ggg gac ggc gac aac atg gtg ccg atg ttc aag tcg        1409
Glu Met Ala Gly Gly Asp Gly Asp Asn Met Val Pro Met Phe Lys Ser
            430                 435                 440 acg gtg gtc cag cag gcg atg cag gaa gcg ggc cag gtg cag atg aag        1457
Thr Val Val Gln Gln Ala Met Gln Glu Ala Gly Gln Val Gln Met Lys
        445                 450                 455 gcg ctg ctc ggc gag gac gcc gaa ccc gag ctg ccc ctg ttc ccc ggt        1505
Ala Leu Leu Gly Glu Asp Ala Glu Pro Glu Leu Pro Leu Phe Pro Gly
    460                 465                 470 ggc ctg gtg acc tcg ccc gaa cgg atg aag tgg ctg cct cac cac cct        1553
Gly Leu Val Thr Ser Pro Glu Arg Met Lys Trp Leu Pro His His Pro
475                 480                 485                 490 gcg tga agcctgtgcg cgccggccgt tcgcgggtgg ccgggacctg cggaacaacc        1609
Ala tatggaaaaa c                                                            1620

<210> SEQ ID NO 2
<211> LENGTH: 491
<212> TYPE: PRT
<213> ORGANISM: Amycolatopsis mediterranei

<400> SEQUENCE: 2

Met Ser Val Glu Asp Phe Asp Val Val Ala Gly Gly Pro Gly
 1               5                  10                  15

Gly Ser Thr Val Ala Thr Leu Val Ala Met Gln Gly His Arg Val Leu
```

-continued

```
                     20                  25                   30
Leu Leu Glu Lys Glu Val Phe Pro Arg Tyr Gln Ile Gly Glu Ser Leu
             35                  40                  45
Leu Pro Ala Thr Val His Gly Val Cys Arg Met Leu Gly Ile Ser Asp
     50                  55                  60
Glu Leu Ala Asn Ala Gly Phe Pro Ile Lys Arg Gly Gly Thr Phe Arg
 65                  70                  75                  80
Trp Gly Ala Arg Pro Glu Pro Trp Thr Phe His Phe Gly Ile Ser Ala
                 85                  90                  95
Lys Met Ala Gly Ser Thr Ser His Ala Tyr Gln Val Glu Arg Ala Arg
                100                 105                 110
Phe Asp Glu Met Leu Leu Asn Asn Ala Lys Arg Lys Gly Val Val Val
            115                 120                 125
Arg Glu Gly Cys Ala Val Thr Asp Val Val Glu Asp Gly Glu Arg Val
        130                 135                 140
Thr Gly Ala Arg Tyr Thr Asp Pro Asp Gly Thr Glu Arg Glu Val Ser
145                 150                 155                 160
Ala Arg Phe Val Ile Asp Ala Ser Gly Asn Lys Ser Arg Leu Tyr Thr
                165                 170                 175
Lys Val Gly Gly Ser Arg Asn Tyr Ser Glu Phe Phe Arg Ser Leu Ala
                180                 185                 190
Leu Phe Gly Tyr Phe Glu Gly Gly Lys Arg Leu Pro Glu Pro Val Ser
            195                 200                 205
Gly Asn Ile Leu Ser Val Ala Phe Asp Ser Gly Trp Phe Trp Tyr Ile
        210                 215                 220
Pro Leu Ser Asp Thr Leu Thr Ser Val Gly Ala Val Val Arg Arg Glu
225                 230                 235                 240
Asp Ala Glu Lys Ile Gln Gly Asp Arg Glu Lys Ala Leu Asn Thr Leu
                245                 250                 255
Ile Ala Glu Cys Pro Leu Ile Ser Glu Tyr Leu Ala Asp Ala Thr Arg
                260                 265                 270
Val Thr Thr Gly Arg Tyr Gly Glu Leu Arg Val Arg Lys Asp Tyr Ser
            275                 280                 285
Tyr Gln Gln Glu Thr Tyr Trp Arg Pro Gly Met Ile Leu Val Gly Asp
        290                 295                 300
Ala Ala Cys Phe Val Asp Pro Val Phe Ser Ser Gly Val His Leu Ala
305                 310                 315                 320
Thr Tyr Ser Ala Leu Leu Ala Ala Arg Ser Ile Asn Ser Val Leu Ala
                325                 330                 335
Gly Asp Leu Asp Glu Lys Thr Ala Leu Asn Glu Phe Glu Leu Arg Tyr
            340                 345                 350
Arg Arg Glu Tyr Gly Val Phe Tyr Glu Phe Leu Val Ser Phe Tyr Gln
        355                 360                 365
Met Asn Val Asn Glu Glu Ser Tyr Phe Trp Gln Ala Lys Lys Val Thr
    370                 375                 380
Gln Asn Gln Ser Thr Asp Val Glu Ser Phe Glu Leu Ile Gly Gly
385                 390                 395                 400
Val Ser Ser Gly Glu Thr Ala Leu Thr Ala Ala Asp Arg Ile Ala Ala
                405                 410                 415
Arg Ser Ala Glu Phe Ala Ala Val Asp Glu Met Ala Gly Gly Asp
            420                 425                 430
Gly Asp Asn Met Val Pro Met Phe Lys Ser Thr Val Val Gln Gln Ala
        435                 440                 445
```

-continued

```
Met Gln Glu Ala Gly Gln Val Gln Met Lys Ala Leu Leu Gly Glu Asp
        450                 455                 460

Ala Glu Pro Glu Leu Pro Leu Phe Pro Gly Gly Leu Val Thr Ser Pro
465                 470                 475                 480

Glu Arg Met Lys Trp Leu Pro His His Pro Ala
        485                 490
```

NUCLEIC ACID FRAGMENT AND VECTOR COMPRISING A HALOGENASE, AND A PROCESS FOR HALOGENATING CHEMICAL COMPOUNDS

The invention relates to a process for the enzymatic halogenation of chemical compounds. The invention further relates to a nucleic acid fragment, a vector and organisms comprising a halogenase or a halogenase gene.

Halogenation reactions have long been known in chemical synthesis. They are used to prepare a large number of halogenated organic compounds. A disadvantage of these synthetic reactions is that special plants are required for the synthesis. These plants must be specially protected against corrosion because the reaction products are frequently very corrosive. There is frequently formation during the synthesis not only of the required product but also of byproducts leading to contamination of the product. If these byproducts cannot be tolerated in the final product, they must undergo elaborate removal. Many byproducts are moreover toxic. Dioxin formation may occur in a number of reactions.

One alternative to chemical halogenation is enzymatic synthesis. It is generally very selective, i.e. generally no byproducts are formed.

The literature discloses enzymes, called haloperoxidases, which halogenate organic compounds in the presence of a halogen ion and hydrogen peroxide. Examples of such enzymes are the haloperoxidase from *Streptomyces aureofaciens* (Kren et al., Liebigs Ann./Red., 1997, 11: 2379–83), from *Rhodococcus erythropolis* (Schrijver et al., Appl. Environ. Microbiol., 1997, 63, 5: 1911–1916), from *Amycolatopsis orientalis* (van Wageningen et al., Chem. Biol., 1998, 5: 155–162), from *Caldariomyces fumago* (Hohaus et al., Angew. Chem. Int. Ed. Engl., 1997, 36, No. 18: 2012–2013), from *Streptomyces lividans* or *Serratia marcescens* (von Pée, K. H., Ann. Rev. Microbiol., 1996, 50: 375–99).

It is not absolutely clear whether the halogenation reaction is the actual enzymatic reaction of these haloperoxidases or whether it is only a side reaction. The enzymes very often show low substrate and cosubstrate affinity and a specificity which is low for enzymes.

Besides the haloperoxidases, other halogenating enzymes are disclosed in the literature. Thus, Kirner et al. (J. Bacteriol., 1998, Vol. 180, No. 7, p. 1939–1943) and Hohaus et al. (Angew. Chem. Int. Ed. Engl., 1997, 36, No. 18, 2012–2013) describe a halogenase which introduces a chlorine atom into position 7 of tryptophan.

Further enzymes are described in Hammer et al. (Appl. Environ. Microbiol., 1997, Vol. 63, No. 6, 2147–2154), de Schrijver et al. (Appl. Environ. Microbiol., 1997, Vol. 63, No. 5, 1911–1916), Nowak-Thompson et al. (J. Bacteriol., 1999, 181: 2166–2174), Solenberg et al. (Chem. Biol., 4, 1997: 195–202) and Dairi et al. (Biosci., Biotechnol. Biochem, 59, 1995, 1099–1106).

A 9.9 kb-long *Amycolatopsis mediterranei* DNA fragment is to be found in GenBank (Y 16952). Pelzer et al. describe two functions for this DNA in the GenBank entry. It codes for oxygenases and glycosyltransferases. No other functions are mentioned.

None of the enzymes has previously been used for the industrial preparation of halogenated organic compounds. It therefore was an object of the present invention to provide an enzyme for the industrial synthesis of halogenated organic compounds.

We have found that this object is achieved by the halogenation process according to the invention, which comprises halogenating a chemical compound in the presence of a halogenase, where the halogenase is (a) encoded by the sequence specified in SEQ ID NO: 1 or a sequence derived therefrom on the basis of the degeneracy of the genetic code, or is (b) encoded by a nucleic acid sequence which codes for a functional fragment on (a) or (c) by a sequence which hybridizes with (a) or (b) under standard conditions, or is (d) encoded by a sequence which has more than 30% identity or more than 60% similarity with the sequence specified under (a).

The halogenase used in the process according to the invention can be isolated from organisms in a manner known to the skilled worker. It can preferably be isolated from organisms which synthesize halogenated compounds, for example glycopeptide antibiotics. Examples of such organisms are to be found among the bacteria and eukaryota such as algae such as Ascophyllum or Synechocystis, lichens, fungi such as Caldariomyces, yeasts and bacteria such as Gram-positive bacteria such as the Actinomycetales, the Bacillales or Gram-negative bacteria such as Pseudomonas. The halogenase can also be isolated advantageously from nocardioform Actinomycetes or Streptomycetes.

It is possible and particularly preferred for the halogenase or halogenases (singular and plural are to be regarded as synonymous hereinafter and for the application) to be isolated from glycopeptide antibiotic-producing members of the family of Pseudonocardiaceae and related bacteria, such as from the genera Pseudonocardia, Saccharomonospora, Saccharopolyspora, Amycolatopsis, Thermocrispum, Pseudoamycolata, Kibdelosporangium, Amycolata, Actinopolyspora, Actinokineospora or Actinobispora, examples which may be mentioned being the genera and species *Nocardia mediterranei*, *Amycolatopsis mediterranei*, *Streptomyces mediterranei*, Nocardia spec., Amycolatopsis spec., Streptomyces spec., *Nocardia orientalis*, *Amycolatopsis orientalis*, *Streptomyces orientalis*, *Streptomyces toyocaensis* or *Streptomyces viridochromogenes*. Mention may very particularly preferably be made of *Amycolatopsis orientalis* C329.4, A82846 and ATCC19795 and *Amycolatopsis mediterranei* DSM 5908. The enzyme can also be isolated advantageously from organisms of the genus Streptomyces, specifically the genus and species *Streptomyces mediterranei*.

The halogenase or the nucleic acid coding for the halogenase can moreover be isolated from the genera Rhodococcus, Thermomonospora, Bacillus, Serratia, Actinosporangium, Actinomadura, Actinoplanes or Micromonospora.

The gene for the halogenase can be isolated from a gene bank from these organisms by various techniques known to the skilled worker. One of these techniques is, for example, the "fishing" for the gene from the gene bank via hybridization with the sequence specified in SEQ ID NO: 1 or parts of this sequence.

An appropriate experimental protocol is to be found, for example, in the textbooks by Sambrook, J. et al. (1989) Molecular cloning: A laboratory manual, Cold Spring, Harbor Laboratory Press, by F. M. Ausubel et al. (1994) Current protocols in molecular biology, John Wiley and Sons, or by D. M. Glover et al., DNA Cloning, Vol. 1 (1995), IRL Press (ISBN 019-963476-9). A further method which may be mentioned is the PCR cloning technique (see examples).

Pelzer et al. (J. Biotechnol., 56 [1997], 115–128) describe in section 2.4 the preparation of a gene (DNA) library for *Amycolatopsis mediterranei*. Further methods for other organisms are known to the skilled worker and can be found in textbooks such as Sambrook et al. (1989).

It is possible in principle to use for the process according to the invention all organisms comprising at least one copy of the halogenase gene.

These may be organisms which naturally contain the gene, or which contain the gene in cloned form. It is moreover possible for the gene to have been introduced into the natural host organism or else into another organism.

Host organisms preferably used are those having an advantageous satisfactory or high tolerance of organic solvents, of the substances to be reacted, of elevated temperatures and of altered pressures. Organisms advantageously used are those into which at least one halogenase gene has been introduced.

Hosts which meet these and other advantageous conditions can be found in virtually all regions of the animal, plant and bacterial kingdoms.

Advantageous microorganisms which can act as host organisms can be found among the fungi, yeasts and bacteria.

Prokaryotic host organisms suitable for the process according to the invention are in principle all Gram-negative or Gram-positive bacteria. Examples of Gram-negative bacteria which may be mentioned are the Enterobacteriaceae such as the genera Escherichia, Aerobacter, Enterobacter, Citrobacter, Shigella, Klebsiella, Serratia, Erwinia or Salmonella or the Pseudomonadaceae such as the genera Pseudomonas, Xanthomonas, Burkholderia, Gluconobacter, Nitrosomonas, Nitrobacter, Methanomonas, Comamonas, Cellulomonas or Acetobacter.

Examples of Gram-positive bacteria which may be mentioned are the endospore-forming Gram-positive aerobic or anaerobic bacteria such as the genera Bacillus, Sporolactobacillus or Clostridium, the coryneform bacteria such as the genera Arthrobacter, Cellulomonas, Curtobacterium, Corynebacterium, Brevibacterium, Microbacterium or Kurthia or the Actinomycetales such as the families Pseudonocardiaceae, Streptomycetaceae or Nocardiaceae with the genera such as Mycobacterium, Rhodococcus, Streptomyces, Nocardia, Amycolatopsis, Pseudonocardia, Saccharomonospora, Saccharopolyspora or Thermocrispum. Bacteria preferably used are those of the genera Escherichia, Salmonella, Pseudomonas, Comamonas, Bacillus, Clostridium, Corynebacterium, Brevibacterium, Streptomyces, Actinomyces, Mycobacterium, Gordona, Micrococcus, Rhodococcus, Nocardia or Amycolatopsis.

Genera and species particularly preferably used are those such as *Escherichia coli, Salmonella typhimurium, Pseudomonas mendocina, Pseudomonas aeruginosa, Pseudomonas mutabilis, Pseudomonas chlororaphis, Pseudomonas fluorescens, Comamonas acidovorans, Comamonas testosteroni, Bacillus subtilis, Bacillus sphaericus, Bacillus stearothermophilus, Bacillus pumilus, Bacillus licheniformis, Bacillus amyloliquefaciens, Bacillus megaterium, Bacillus cereus, Bacillus thuringiensis*, Streptomyces sp., *Streptomyces lividans, Amycolatopsis mediterranei, Amycolatopsis orientalis, Nocardia mediterranei* or *Nocardia orientalis*.

The organisms advantageously used are those for which the methods necessary for introducing genetic information are already available, such as for Escherichia, Bacillus, Pseudomonas, Streptomyces, Nocardia or Amycolatopsis.

The taxonomic position of the genera mentioned has been subject in recent years to great changes and is still in flux because incorrect genus and species names are being corrected. Owing to this taxonomic regrouping, which has frequently been necessary in the past, of the genera mentioned within the classification of bacteria, also suitable for the process according to the invention are families, genera and species other than those mentioned above, both as initial organism for isolating the halogenase or the halogenase gene, and for introducing the DNA.

Suitable eukaryotic host organisms in the process according to the invention are in principle all organisms such as fungi, yeasts, plants, plant cells or animal cells. Yeasts which may preferably be mentioned are the genera Rhodotorula, Yarrowia, Sporobolomyces, Candida, Hansenula, Pichia, Saccharomyces or Schizosaccharomyces. Particularly preferred genera and species are *Rhodotorula rubra, Rhodotorula glutinis, Rhodotorula graminis, Yarrowia lipolytica, Sporobolomyces salmonicolor, Sporobolomyces shibatamus, Saccharomyces cerevisiae, Candida boidinii, Candida bombicola, Candida cylindracea, Candida parapsilosis, Candida rugosa, Candida tropicalis, Pichia methanolica* or *Pichia pastoris*.

Examples of fungi which may be mentioned are Aspergillus, Canninghamella, Beauveria, Mucor, Neurospora, Penicillium or Rhizoctonia. Fungi advantageously used in the process according to the invention are of the following genus and species: *Aspergillus awamori, Aspergillus candidus, Aspergillus ficuum, Aspergillus flavus, Aspergillus niger, Aspergillus terreus, Beauveria bassiana, Beauveria brongniartii, Beauveria densa, Beauveria nivea, Mucor miehei, Mucor rouxii*, Mucor sp., *Neurospora crassa, Penicillium chrysogenum, Penicillium notatum, Rhizoctonia repens* or *Rhizoctonia solani*.

Also suitable are plants such as *Arabidopsis thaliana* or *Lavendula vera*. Plant cell cultures, protoplasts from plants or callus cultures are particularly preferred.

In the process according to the invention, a chemical compound as described above is converted in the presence of a halogenase into the corresponding halogenated compound.

The halogenase is in this case (a) encoded by the sequence specified in SEQ ID NO: 1 or a sequence derived therefrom on the basis of the degeneracy of the genetic code, or is (b) encoded by a nucleic acid sequence which codes for a functional fragment of (a) or (c) by a sequence which hybridizes with (a) or (b) under standard conditions, or is (d) encoded by a sequence which has more than 30% identity or more than 60% similarity with the sequence specified under (a).

These sequences specified under (a) to (d) can in principle be introduced into the organisms used by all methods known to the skilled worker, but they are advantageously introduced into the organisms or their cells by transformation, transfection, electroporation, using the particle gun or by microinjection. Methods appropriate for microorganisms can be found by the skilled worker in the textbooks by Sambrook, J. et al. (1989) Molecular cloning: A laboratory manual, Cold Spring Harbor Laboratory Press, by F. M. Ausubel et al. (1994) Current protocols in molecular biology, John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Harbor Laboratory Press or Guthrie et al. Guide to Yeast Genetics and Molecular Biology, Methods in Enzymology, 1994, Academic Press.

Transfer of foreign genes into the genome of a plant is likewise referred to as transformation. In this case, the methods described for transformation and regeneration of plants from plant tissues or plant cells for transient or stable transformation are utilized. Suitable methods are protoplast transformation by polyethylene glycol-induced DNA uptake, the use of a gene gun, electroporation, incubation of dry embryos in DNA-containing solution, microinjection and Agrobacterium-mediated gene transfer. Said processes are described, for example, in B. Jenes et al., Techniques for Gene Transfer, in: Transgenic Plants, Vol. 1, Engineering and Utilization, edited by S. D. Kung and R. Wu, Academic Press (1993), 128–143, and in Potrykus, Annu. Rev. Plant Physiol. Plant Molec. Biol. 42 (1991) 205–225. The construct to be expressed is preferably cloned into a vector which is suitable for transforming *Agrobacterium tumefaciens*, for example pBin19 (Bevan et al., Nucl. Acids Res. 12 (1984) 8711). The transformation of plants with *Agrobacterium tumefaciens* is described, for example, by Höfgen and Willmitzer in Nucl. Acids Res. (1988) 16, 9877.

The genetically modified plant cells can be regenerated by all methods known to the skilled worker. Appropriate methods can be found in the abovementioned publications by S. D. Kung and R. Wu, Potrykus or Höfgen and Willmitzer.

The nucleic acid introduced into the organisms can moreover be present in the organisms as extrachromosomal element or integrated into the genome.

Integration into the genome can take place, for example, by heterologous or homologous recombination.

The nucleic acids are advantageously cloned together with at least one reporter gene into a DNA construct which is introduced into the organisms. This reporter gene ought to make easy detection possible by a growth, fluorescence, chemoluminescence or bioluminescence assay or by a photometric measurement. Examples of reporter genes which may be mentioned are hydrolase genes, fluorescent protein genes, bioluminescence genes, glucosidase genes, peroxidase gene or genes such as the luciferase gene, β-galactosidase gene, gfp gene, lipase gene, esterase gene, peroxidase gene, β-lactamase gene, acetyltransferase, phosphotransferase or adenyltransferase gene. These genes make easy measurement and quantification of the transcription activity and thus the expression of the genes possible.

In place of the reporter genes or gene, however, it is also possible and advantageous to use an antibiotic or other resistance gene or a biosynthesis gene.

Pelzer et al. describe a special gene cloning system for the glycopeptide antibiotic-producer *Amycolatopsis mediterranei*, specifically for the strain DSM5908.

Pelzer et al. describe a modified direct transformation process for introducing DNA. The efficiency of DNA uptake depends on the age of the culture. The best results can be achieved with mycelium from the early stationary phase (52 to 55 hours). The paper by Pelzer et al. (J. Biotechnol. 56 [1997], 115–128) is incorporated herein by reference.

Further advantageous methods which may be mentioned by way of example for introducing nucleic acids into, for example, Actinomycetes such as Streptomycetes are conjugation (Muth, G., Brolle, D. F., Wohlleben, W., 1999, Genetics of Streptomyces. In "Manual of Industrial Microbiology and Biotechnology", Eds. Demain, A. L. and Davies, J. E., ASM Press, Washington, D.C.), and PEG-induced protoplast transformation (Hopwood, D. A. et al., 1985, Genetic manipulation of Streptomyces; a laboratory manual, The John Innes Foundation, Norwich, U.K. und W. Wohlleben and G. Muth, 1993, Streptomyces plasmid vectors, p. 147–175. In K. G. Harley, ed., Plasmids: A practical approach, Oxford University Press, Oxford and Muth, G., Brolle, D. F., Wohlleben, W., 1999, see above). Both methods can, as is well known to the skilled worker, easily be applied to other Actinomycetales strains.

To bypass the strong restriction system which is often present in Actinomycetes, it is advantageous to convert the nucleic acid which is to be transformed, before the actual transformation, into single-stranded DNA by thermal denaturation in the presence or absence of the phage f1 origin (Hillemann et al., 1991, Nucleic Acids Res. 194, 727–731) or by alkaline denaturation/renaturation (Oh and Chater, 1997, J. Bacteriol., 179, 122–127).

To bypass the restriction by the host organism, it is possible in particular with Actinomycetes advantageously to transfer the DNA by interspecific conjugation of, for example, *Escherichia coli* to Actinomycetes. Even rare Actinomyces strains are accessible in this way (Baltz, R. H., 1998, Trends in Microbiology, 6, 76,83, Flett et al., 1997, FEMS Microbiol. Lett., 155, 223–229). It is also possible by electroporation advantageously to introduce nucleic acids into Actinomyces strains (Muth, G., Brolle, D. F., Wohlleben, W., 1999, see above; English et al., 1998, J. Ind. Microbiology and Biotechnology, 21, 219–224; Lal, R. et al., 1991, Appl. Environ. Microbiol. 57, 665–671). Mention may also be made of electroduction, as an advantageous variant of electroporation. It makes it possible for DNA to be transferred rapidly and directly from *E. coli* to Actinomycetes by electroporation using shuttle vectors (Muth, G., Brolle, D. F., Wohlleben, W., 1999).

Besides single cells it is also possible and advantageous to transform mycelium in the Amycolatopsis and Nocardia with addition of $CsCl_2$, calf thymus DNA and PEG (Pelzer et al., 1997; Madon J. and R. Hütter, 1991, J. Bacteriol., 173, 6325–6331, Vrijbloed, J. W. et al., 1995, Plasmid 34, 96–104; Kumar, C. V. et al., 1995, Appl. Environ. Microbiol. 60, 4086–4093).

A nucleic acid sequence which codes for a functional fragment of (a) means sequences which are shorter than (a) but still have the enzymatic activity. These sequences may have been truncated at the 3' or 5' end of the sequence. It is also possible for parts to have been deleted within the coding sequence in the reading frame without losing the enzymatic activity.

As a rule, the functional fragments are truncated by 5 to 30%, preferably by 10 to 20%, compared with sequence (a). Sequences longer than sequence (a) are also theoretically conceivable.

Sequences which hybridize under standard conditions with the sequences specified under (a) and (b) mean sequences which hybridize, for example, at temperatures between 42 and 58° C. in an aqueous buffer solution with a concentration between 0.1 and 5×SSC (1×SSC 0.15 M NaCl, 15 mM sodium citrate; pH 7.2) or additionally in the presence of 50% formamide, such as 42° C. in 5×SSC and 50% formamide.

The experimental conditions for the DNA hybridization are to be found in relevant genetics textbooks such as Sambrook et al., "Molecular Cloning", Cold Spring Harbor Laboratory, 1989.

It is advantageous to use for the hybridization short specific oligonucleotides with a length of at least 20 to 25 nucleotides. Oligonucleotides comprising at least 25 nucleotides are preferably used. However, it is also possible and advantageous to use longer oligonucleotides comprising 50 to 200 nucleotides or even longer portions up to the complete nucleic acid sequence [see (a) and (b)].

Nucleic acids in the process according to the invention mean, for example, DNA, cDNA, RNA or mRNA. They also include the homologs of these nucleic acid sequences.

Homologs mean, for example, the eukaryotic or prokaryotic homologs, truncated sequences or single-stranded DNA. These may be homologous with the coding or non-coding sequence.

It is also possible and advantageous to use for the process according to the invention halogenases which are encoded by a sequence which has more than 30%, preferably 50%, particularly preferably 60%, very particularly preferably more than 95%, identity, or more than 60%, preferably 70%, particularly preferably 80%, very particularly preferably 97%, similarity with the sequence specified in SEQ ID NO: 1, over the entire length at the level of the amino acid derived from the sequence (Blast program, W. Gish and D. J. States, Nat. Genet., 3, 1993: 266–272).

These sequences are advantageously obtainable from SEQ ID NO: 1 by deletion, insertion and/or substitution of nucleotides, with retention in this and in all other cases of the enzymatic activity of the halogenase proteins derived from the sequences.

In the process according to the invention, chemical compounds of the following general structure I are advantageously converted using the abovementioned halogenase:

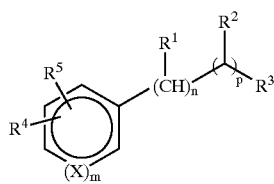

(I)

where the variables and substituents in formula I have the following meanings:

$R^1$=hydrogen, hydroxyl, substituted or unsubstituted, branched or unbranched $C_1$–$C_{10}$-alkyl, $C_2$–$C_{10}$-alkenyl, $C_1$–$C_{10}$-alkoxy-, $C_2$–$C_{10}$-alkenyloxy-, $R^6R^7N$—,

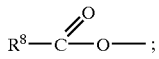

$R^2$=hydrogen, hydroxyl, substituted or unsubstituted, branched or unbranched $C_1$–$C_{10}$-alkyl, $C_1$–$C_{10}$-alkoxy, $C_2$–$C_{10}$-alkenyl, $C_2$–$C_{10}$-alkenyloxy, $R^6R^7N$—;

$R^3$=hydrogen, hydroxyl, substituted or unsubstituted, branched or unbranched $C_1$–$C_{10}$-alkyl, $C_1$–$C_{10}$-alkoxy, $C_2$–$C_{10}$-alkenyl, $C_2$–$C_{10}$-alkenyloxy, $C_1$–$C_{10}$-alkylcarbonyl, $C_2$–$C_{10}$-alkenylcarbonyl, aryl, hetaryl,

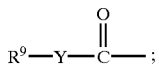

$R^4$ and $R^5$ independently of one another hydrogen, hydroxyl, halogen, nitro, cyano, substituted or unsubstituted, branched or unbranched $C_1$–$C_{10}$-alkyl, $C_1$–$C_{10}$-alkoxy, $C_2$–$C_{10}$-alkenyl, $C_2$–$C_{10}$-alkenyloxy, substituted or unsubstituted $C_3$–$C_{10}$-cycloalkyl, aryl, hetaryl, $R^6R^7N$—, and where two radicals $R^4$ and $R^5$ on adjacent carbon atoms may together form another substituted or unsubstituted aromatic, saturated or partially saturated ring with 5 to 6 atoms in the ring which may contain one or more heteroatoms such as O, N or S;

$R^6$ and $R^7$ independently of one another hydrogen or substituted or unsubstituted, branched or unbranched C–$C_{10}$-alkyl;

$R^8$=substituted or unsubstituted, branched or unbranched $C_1$–$C_{10}$-alkyl, $C_2$–$C_{10}$-alkenyl, substituted or unsubstituted aryl;

$R^9$=substituted or unsubstituted, branched or unbranched $C_1$–$C_{10}$-alkyl, $C_2$–$C_{10}$-alkenyl, substituted or unsubstituted aryl, hetaryl;

X=—CH— or N;
Y=O or N;
m=0 or 1;
n=0, 1, 2 or 3;
p=0 or 1.

The compounds of the general formula I are converted in the presence of the halogenase into the halogenated compounds of the following general formula II:

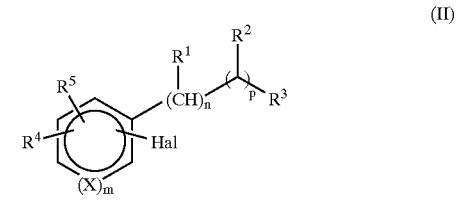

(II)

where the variables and substituents in formula II have the meanings specified for formula I, and Hal is chlorine, fluorine, bromine or iodine, preferably chlorine or bromine.

As a rule, sufficient halogen atoms for the reaction are present in the reaction solution. However, it is advantageous to add a halogen donor to the reaction solution.

It is possible in principle to use as halogen donor all halogen-containing organic or inorganic compounds. For the sake of simplicity and for reasons of cost, inorganic compounds are preferred. Halogens are advantageously added in the form of their salts to the reaction solution. Examples which may be mentioned are the alkali metal and/or alkaline earth metal salts of the halogens.

$R^1$ in the compounds of the formula (=structure) I and II is hydrogen, hydroxyl, substituted or unsubstituted, branched or unbranched $C_1$–$C_{10}$-alkyl, $C_2$–$C_{10}$-alkenyl, $C_1$–$C_{10}$-alkoxy, $C_2$–$C_{10}$-alkenyloxy, $R^6R^7N$—,

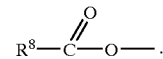

Alkyl radicals which may be mentioned are substituted or unsubstituted branched or unbranched $C_1$–$C_{10}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Methyl, ethyl, n-propyl, n-butyl, i-propyl or i-butyl are preferred. Methyl and ethyl are particularly preferred.

Alkenyl radicals which may be mentioned are substituted or unsubstituted, branched or unbranched $C_2$–$C_{10}$-alkenyl chains such as ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl or 9-decenyl, and the branched-chain homologs thereof.

Alkoxy radicals which may be mentioned are substituted or unsubstituted, branched or unbranched $C_1$–$C_{10}$-alkoxy chains such as methoxy, ethoxy, propxy, 1-methylethoxy, butoxy, 1-methylpropoxy, 2-methylpropoxy, 1,1-dimethylethoxy, pentoxy, 1-metylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, hexyloxy, heptyloxy, octyloxy, nonyloxy or decyloxy and the branched-chain homologs thereof.

Alkenyloxy radicals which may be mentioned are substituted or unsubstituted, branched or unbranched $C_2$–$C_{10}$-alkenyloxy chains such as ethenyloxy, propenyloxy, 1-butenyloxy, 2-butenyloxy, 3-butenyloxy, 2-methylpropenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy, 1-ethyl-2-methyl-2-propenyloxy, 1-heptenyloxy, 2-heptenyloxy, 3-heptenyloxy, 4-heptenyloxy, 5-heptenyloxy, 6-heptenyloxy, 1-octenyloxy, 2-octenyloxy, 3-octenyloxy, 4-octenyloxy, 5-octenyloxy, 6-octenyloxy, 7-octenyloxy, 1-nonenyloxy, 2-nonenyloxy, 3-nonenyloxy, 4-nonenyloxy, 5-nonenyloxy, 6-nonenyloxy, 7-nonenyloxy, 8-nonenyloxy, 1-decenyloxy, 2-decenyloxy, 3-decenyloxy, 4-decenyloxy, 5-decenyloxy, 6-decenyloxy, 7-decenyloxy, 8-decenyloxy or 9-decenyloxy, and the branched-chain homologs thereof.

Substituents suitable for said $R^1$ radicals are in principle all conceivable substituents which do not impede the halogenase reaction, for example one or more substituents such as halogen, such a fluorine, chlorine or bromine, cyano, nitro, amino, hydroxyl, alkyl, cycloalkyl, aryl, alkoxy, benzyloxy, phenyl or benzyl.

$R^2$ in the compounds of the formula I and II is hydrogen, hydroxyl, substituted or unsubstituted, branched or unbranched $C_1$–$C_{10}$-alkyl, $C_1$–$C_{10}$-alkoxy, $C_2$–$C_{10}$-alkenyl, $C_2$–$C_{10}$-alkenyloxy, $R^6R^7N$—;

Alkyl radicals which may be mentioned are substituted or unsubstituted branched or unbranched $C_1$–$C_{10}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Methyl, ethyl, n-propyl, n-butyl, i-propyl or i-butyl are preferred.

Alkenyl radicals which may be mentioned are substituted or unsubstituted, branched or unbranched $C_2$–$C_{10}$-alkenyl chains such as ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl or 9-decenyl, and the branched-chain homologs thereof.

Alkoxy radicals which may be mentioned are substituted or unsubstituted, branched or unbranched $C_1$–$C_{10}$-alkoxy chains such as methoxy, ethoxy, propoxy, 1-methylethoxy, butoxy, 1-methylpropoxy, 2-methylpropoxy, 1,1-dimethylethoxy, pentoxy, 1methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, hexyloxy, heptyloxy, octyloxy, nonyloxy or decyloxy and the branched-chain homologs thereof.

Alkenyloxy radicals which may be mentioned are substituted or unsubstituted, branched or unbranched $C_2$–$C_{10}$-alkenyloxy chains such as ethenyloxy, propenyloxy, 1-butenyloxy, 2-butenyloxy, 3-butenyloxy, 3-methylpropenyloxy, 1-pentenyloxy, 2-pentenyloxy, 3-pentyenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenzyloxy, 2,3-dimethyl-3-butenyloxy, 3,3-dimethyl-1-butyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy, 1-ethyl-2-methyl-2-propenyloxy, 1-heptenyloxy, 2-heptenyloxy, 3-heptenyloxy, 4-heptenyloxy, 5-heptenyloxy, 6-heptenyloxy, 1-octenyloxy, 2-octenyloxy, 3-octenyloxy, 4-octenyloxy, 5-octenyloxy, 6-octenyloxy, 7-octenyloxy, 1-nonenyloxy, 2-nonenyloxy, 3-nonenyloxy, 4-nonenyloxy, 5-nonenyloxy, 6-nonenyloxy, 7-nonenyloxy, 8-nonenyloxy, 1-decenyloxy, 2-decenyloxy, 3-decenyloxy, 4-decenyloxy, 5-decenyloxy, 6-decenyloxy, 7-decenyloxy, 8-decenyloxy or 9-decenyloxy, and the branched-chain homologs thereof.

Substituents suitable for said $R^2$ radicals are in principle all conceivable substituents which do not impede the halogenase reaction, for example one or more substituents such as halogen, such as fluoride, chlorine or bromine, cyano, nitro, amino, hydroxyl, alkyl, cycloalkyl, aryl, alkoxy, benzyloxy, phenyl or benzyl.

$R^3$ in the compounds of the formula I and II is hydrogen, hydroxyl, substituted or unsubstituted, branched or unbranched $C_1$–$C_{10}$-alkyl, $C_1$–$C_{10}$-alkoxy, $C_2$–$C_{10}$-alkenyl, $C_2$–$C_{10}$-alkenyloxy, $C_1$–$C_{10}$-alkylcarbonyl, $C_2$–$C_{10}$-alkenylcarbonyl, aryl, hetaryl,

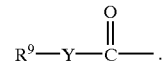

Alkyl radicals which may be mentioned are substituted or unsubstituted branched or unbranched $C_1$–$C_{10}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Methyl, ethyl, n-propyl, n-butyl, i-propyl or i-butyl are preferred.

Alkenyl radicals which may be mentioned are substituted or unsubstituted, branched or unbranched $C_2$–$C_{10}$-alkenyl chains such as ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl or 9-decenyl, and the branched-chain homologs thereof.

Alkoxy radicals which may be mentioned are substituted or unsubstituted, branched or unbranched $C_1$–$C_{10}$-alkoxy chains such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2- dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy 1-ethyl-1-methylpropoxy, 1-ethyl-2-methoxypropoxy, hexyloxy, heptyloxy, octyloxy, nonyloxy or decyloxy and the branched-chain homologs thereof.

Alkenyloxy radicals which may be mentioned are substituted or unsubstituted, branched or unbranched $C_2$–$C_{10}$-alkenyloxy chains such as ethenyloxy, propenyloxy, 1-butenyloxy, 2-butenyloxy, 3-butenyloxy, 2-methylpropenyloxy, 1-pentenyloxy, 2-pentenyloxy, 3-pentenyloxy, 3-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-1-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy, 1-ethyl-2-methyl-2-propenyloxy, 1-heptenyloxy, 2-heptenyloxy, 3-heptenyloxy, 4-heptenyloxy, 5-heptenyloxy, 6-heptenyloxy, 1-octenyloxy, 2-octenyloxy, 3-octenyloxy, 4-octenyloxy, 5-octenyloxy, 6-octenyloxy, 7-octenyloxy, 1-nonenyloxy, 2-nonenyloxy, 3-nonenyloxy, 4-nonenyloxy, 5-nonenyloxy, 6-nonenyloxy, 7-nonenyloxy, 8-nonenyloxy, 1-decenyloxy, 2-decenyloxy, 3-decenyloxy, 4-decenyloxy, 5-decenyloxy, 6-decenyloxy, 7-decenyloxy, 8-decenyloxy or 9-decenyloxy, and the branched-chain homologs thereof.

Alkylcarbonyl radicals which may be mentioned are branched or unbranched $C_1$–$C_{10}$-alkylcarbonyl chains such as methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, n-hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl, 1-ethyl-2-methylpropylcarbonyl, n-heptylcarbonyl, n-octylcarbonyl, n-nonylcarbonyl or n-decylcarbonyl.

Alkenylcarbonyl radicals which may be mentioned are branched or unbranched $C_2$–$C_{10}$-alkenylcarbonyl chains such as ethylcarbonyl, propenylcarbonyl, 1-butenylcarbonyl, 2-butenylcarbonyl, 3-butenylcarbonyl, 2-methylpropenylcarbonyl, 1-pentenylcarbonyl, 2-pentenylcarbonyl, 3-pentenylcarbonyl, 4-pentenylcarbonyl, 1-methyl-1-butenylcarbonyl, 2-methyl-1-butenylcarbonyl, 3-methyl-1-butenylcarbonyl, 1-methyl-2-butenylcarbonyl, 2-methyl-2-butenylcarbonyl, 3-methyl-2-butenylcarbonyl, 1-methyl-3-butenylcarbonyl, 2-methyl-3-butenylcarbonyl, 3-methyl-3-butenylcarbonyl, 1,1-dimethyl-2-propenylcarbonyl, 1,2-dimethyl-1-propenylcarbonyl, 1,2-dimethyl-2-propenylcarbonyl, 1-ethyl-1-propenylcarbonyl, 1-ethyl-2-propenylcarbonyl, 1-hexenylcarbonyl, 2-hexenylcarbonyl, 3-hexenylcarbonyl, 4-Hexenylcarbonyl, 5-Hexenylcarbonyl, 1-methyl-1-pentenylcarbonyl, 2-methyl-1-pentenylcarbonyl, 3-methyl-1-pentenylcarbonyl, 4-methyl-1-pentenylcarbonyl, 1-methyl-2-pentenylcarbonyl, 2-methyl-2-pentenylcarbonyl, 3-methyl-2-pentenylcarbonyl, 4-methyl-2-pentenylcarbonyl, 1-methyl-3-pentenylcarbonyl, 2-methyl-3-pentenylcarbonyl, 3-methyl-3-pentenylcarbonyl, 4-methyl-3-pentenylcarbonyl, 1-methyl-4-pentenylcarbonyl, 2-methyl-4-pentenylcarbonyl, 3-methyl-4-pentenylcarbonyl, 4-methyl-4-pentenylcarbonyl, 1,1-dimethyl-2-butenylcarbonyl, 1,1-dimethyl-3-butenylcarbonyl, 1,2-dimethyl-1-butenylcarbonyl, 1,2-dimethyl-2-butenylcarbonyl, 1,2-dimethyl-3-butenylcarbonyl, 1,3-dimethyl-1-butenylcarbonyl, 1,3-dimethyl-2-butenylcarbonyl, 1,3-dimethyl-3-butenylcarbonyl, 2,2-dimethyl-3-butenylcarbonyl, 2,3-dimethyl-1-butenylcarbonyl, 2,3-dimethyl-2-butenylcarbonyl, 2,3-dimethyl-3-butenylcarbonyl, 3,3-dimethyl-1-butenylcarbonyl, 3,3-dimethyl-2-butenylcarbonyl, 1-ethyl-1-butenylcarbonyl, 1-ethyl-2-butenylcarbonyl, 1-ethyl-3-butenylcarbonyl, 2-ethyl-1-butenylcarbonyl, 2-ethyl-2-butenylcarbonyl, 2-ethyl-3-butenylcarbonyl, 1,1,2-trimethyl-2-propenylcarbonyl, 1-ethyl-1-methyl-2-propenylcarbonyl, 1-ethyl-2-methyl-1-propenylcarbonyl, 1-ethyl-2-methyl-2-propenylcarbonyl, 1-heptenylcarbonyl, 2-heptenylcarbonyl, 3-heptenylcarbonyl, 4-heptenylcarbonyl, 5-heptenylcarbonyl, 6-heptenylcarbonyl, 1-octenylcarbonyl, 2-octenylcarbonyl, 3-octenylcarbonyl, 4-octenylcarbonyl, 5-octenylcarbonyl, 6-octenylcarbonyl, 7-octenylcarbonyl, nonenylcarbonyl or decenylcarbonyl.

Substituents suitable for said $R^3$ radicals are in principle all conceivable substituents which do not impede the halogenase reaction, for example one or more substituents such as halogen, such as fluorine, chlorine or bromine, cyano, nitro, amino, hydroxyl, alkyl, cycloalkyl, aryl, alkoxy, benzyloxy, phenyl or benzyl.

Examples of aryl radicals which may be mentioned are, for example, phenyl, methoxyphenyl or naphthyl or aromatic rings or ring systems having 6 to 18 carbon atoms in the ring system and up to 24 other carbon atoms which may form further nonaromatic rings or ring systems having 3 to 8 carbon atoms in the ring, which may optionally be substituted by one or more radicals such as halogen, such as fluorine, chlorine or bromine, cyano, nitro, amino, hydroxyl, alkyl, alkoxy, or other radicals. Optionally substituted phenyl, methoxyphenyl and naphthyl are preferred.

Hetaryl radicals which may be mentioned are simple or fused aromatic ring systems having one or more heteroaromatic 3- to 7-membered rings, which may contain one or more heteroatoms such as N, O or S, and which may optionally be substituted by one or more radicals such as halogen such as fluorine, chlorine or bromine, cyano, nitro, amino, hydroxyl, mercapto alkyl, alkoxy or other aromatic or other saturated or unsaturated nonaromatic rings or ring systems.

$R^4$ and $R^5$ in the compounds of the formula I and II are, independently of one another, hydrogen, hydroxyl-, halogen, nitro, cyano, substituted or unsubstituted, branched or unbranched $C_1$–$C_{10}$-alkyl, $C_1$–$C_{10}$-alkoxy, $C_2$–$C_{10}$-alkenyl, $C_2$–$C_{10}$-alkenyloxy, substituted or unsubstituted $C_3$–$C_{10}$-cycloalkyl, aryl, hetaryl, $R^6R^7N$—, and where two $R^4$ and $R^5$ radicals on adjacent carbon atoms may together form another substituted or unsubstituted aromatic, saturated or partly saturated ring having 5 to 6 atoms in the ring, which may contain one or more heteroatoms such as O, N or S.

Halogen is fluorine, bromine or chlorine, preferably chlorine.

Alkyl radicals which may be mentioned are substituted or unsubstituted branched or unbranched $C_1$–$C_{10}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Methyl, ethyl, n-propyl, n-butyl, i-propyl or i-butyl are preferred.

Alkenyl radicals which may be mentioned are substituted or unsubstituted, branched or unbranched $C_2$–$C_{10}$-alkenyl chains such as ethenyl, propenyl, 1-butenyl, 2-butenyl, 3-butenyl, 2-methoxypropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl , 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl or 9-decenyl, and the branched-chain homologs thereof.

Alkoxy radicals which may be mentioned are substituted or unsubstituted, branched or unbranched $C_1$–$C_{10}$-alkoxy chains such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, hexyloxy, heptyloxy, octyloxy, nonyloxy or decyloxy and the branched-chain homologs thereof.

Alkenyloxy radicals which may be mentioned are substituted or unsubstituted, branched or unbranched $C_2$–$C_{10}$-alkenyloxy chains such as ethenyloxy, propenyloxy, 1-butenyloxy, 2-butenyloxy, 3-butenyloxy, 2-methylpropenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy, 1-ethyl-2-methyl-2-propenyloxy, 1-heptenyloxy, 2-heptenyloxy, 3-heptenyloxy, 4-heptenyloxy, 5-heptenyloxy, 6-heptenyloxy, 1-octenyloxy, 2-octenyloxy, 3-octenyloxy, 4-octenyloxy, 5-octenyloxy, 6-octenyloxy, 7-octenyloxy, 1-nonenyloxy, 2-nonenyloxy, 3-nonenyloxy, 4-nonenyloxy, 5-nonenyloxy, 6-nonenyloxy, 7-nonenyloxy, 8-nonenyloxy, 1-decenyloxy, 2-decenyloxy, 3-decenyloxy, 4-decenyloxy, 5-decenyloxy, 6-decenyloxy, 7-decenyloxy, 8-decenyloxy or 9-decenyloxy, and the branched-chain homologs thereof.

Examples of cycloalkyl radicals which may be mentioned are substituted or unsubstituted branched or unbranched $C_3$–$C_{10}$-cycloalkyl chains having 3 to 7 carbon atoms in the ring or ring system such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1- butylcyclopropyl, 1,2-dimethylcyclopropyl, 1-methyl-2-ethylcyclopropyl, cyclooctyl, cyclononyl or cyclodecyl. The cycloalkyl radicals may also contain heteroatoms such as S, N and O in the ring.

Aryl means, for example, simple or fused aromatic ring systems which may optionally be substituted by one or more radicals such as halogen such as fluorine, chlorine or bromine, cyano, nitro, amino, hydroxyl, mercapto, alkyl, alkoxy, aryl, hetaryl or other saturated or unsaturated non-aromatic rings or ring systems. Optionally substituted phenyl, methoxyphenyl and naphthyl are preferred.

Hetaryl means, for example, simple or fused aromatic ring systems having one or more heteroaromatic 3- to 7-membered rings which may contain one or more heteroatoms such as N, O or S, and which may optionally be substituted by one or more radicals such as halogen such as fluorine, chlorine or bromine, cyano, nitro, amino, hydroxyl, mercapto, alkyl, alkoxy or other aromatic or other saturated or unsaturated nonaromatic rings or ring systems.

Substituents suitable for said $R^4$ and $R^5$ radicals are in principle all conceivable substituents, for example one or more substituents such as halogen, such as fluorine, chlorine or bromine, cyano, nitro, amino, hydroxyl, alkyl, cycloalkyl, aryl, alkoxy, benzyloxy, phenyl or benzyl.

$R^6$ and $R^7$ in the substituent $R^6R^7N$— are, independently of one another, hydrogen or substituted or unsubstituted, branched or unbranched $C_1$–$C_{10}$-alkyl.

Alkyl radicals which may be mentioned are substituted or unsubstituted branched or unbranched $C_1$–$C_{10}$-alkyl chains such as methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Methyl, ethyl, n-propyl, n-butyl, i-propyl or i-butyl are preferred.

Substituents suitable for said $R^6$ and $R^7$ radicals are principle all conceivable substituents which do not impede the halogenase reaction, for example one or more substituents such as halogen, such as fluorine, chlorine or bromine, cyano, nitro, amino, hydroxyl, alkyl, cycloalkyl, aryl, alkoxy, benzyloxy, phenyl or benzyl.

$R^8$ in the substituent

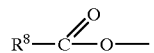

is substituted or unsubstituted, branched or unbranched $C_1$–$C_{10}$-alkyl, $C_2$–$C_{10}$-alkenyl, substituted or unsubstituted aryl.

Alkyl radicals which may be mentioned are substituted or unsubstituted branched or unbranched $C_1$–$C_{10}$-alkyl chains such as methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Methyl, ethyl, n-propyl, n-butyl, i-propyl or i-butyl are preferred.

Alkenyl radicals which may be mentioned are substituted or unsubstituted, branched or unbranched $C_2$–$C_{10}$-alkenyl chains such as ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl or 9-decenyl, and the branched-chain homologs thereof.

Aryl means, for example, simple or fused aromatic ring systems which may optionally be substituted by one or more radicals such as halogen such as fluorine, chlorine or bromine, cyano, nitro, amino, hydroxyl, mercapto, alkyl, alkoxy, aryl, hetaryl or other saturated or unsaturated non-aromatic rings or ring systems. Optionally substituted phenyl, methoxyphenyl and naphthyl are preferred.

$R^9$ is the substituent

is substituted or unsubstituted, branched or unbranched $C_1$–$C_{10}$-alkyl, $C_2$–$C_{10}$-alkenyl, substituted or unsubstituted aryl, hetaryl.

Alkyl radicals which may be mentioned are substituted or unsubstituted branched or unbranched $C_1$–$C_{10}$-alkyl chains such as methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Methyl, ethyl, n-propyl, n-butyl, i-propyl or i-butyl are preferred.

Alkenyl radicals which may be mentioned are substituted or unsubstituted, branched or unbranched $C_2$–$C_{10}$-alkenyl chains such as ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-2-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl or 9-decenyl, and the branched-chain homologs thereof.

Aryl means, for example, simple or fused aromatic ring systems which may optionally be substituted by one or more radicals such as halogen such as fluorine, chlorine or bromine, cyano, nitro, amino, hydroxyl, mercapto, alkyl, alkoxy, aryl, hetaryl or other saturated or unsaturated non-aromatic rings or ring systems. Optionally substituted phenyl, methoxyphenyl and naphthyl are preferred.

Hetaryl means, for example, simple or fused aromatic ring systems having one or more heteroaromatic 3- to 7-membered rings which may contain one or more heteroatoms such as N, O or S, and which may optionally be substituted by one or more radicals such as halogen such as fluorine, chlorine or bromine, cyano, nitro, amino, hydroxyl, mercapto, alkyl, alkoxy or other aromatic or other saturated or unsaturated nonaromatic rings or ring systems.

Substituents suitable for said $R^8$ and $R^9$ radicals are in principle all conceivable substituents which do not impede the halogenase reaction, for example one or more substituents such as halogen, such as fluorine, chlorine or bromine, cyano, nitro, amino, hydroxyl, alkyl, cycloalkyl, aryl, alkoxy, benzyloxy, phenyl or benzyl.

It is possible to use for the process according to the invention an organism which comprises at least one gene for the halogenase described above. A microorganism is preferably used.

The process can advantageously be carried out with a crude extract of a halogenase-containing organism or with a partially or completely purified enzyme.

As described above, it is advantageous to add a halogen donor to the reaction. Halogen preferably means chlorine or bromine. Fluorine and iodine are less preferred because they may have toxic effects, so that the organisms have their activity impaired or are even killed. The reaction is, however, also possible with fluorine and iodine.

The process according to the invention can be carried out with growing or resting cells.

For halogenation with growing organisms, the organisms used for the halogenation are cultured in a medium which makes it possible for these organisms, preferably microorganisms, to grow.

This medium may be a synthetic or a natural complex medium. The media used will be those known to the skilled worker and appropriate for the organism. The media used for growth of the microorganisms normally contain a carbon source, a nitrogen source, inorganic salts and, where appropriate, small amounts of vitamins and trace elements.

Examples of advantageous carbon sources are sugars such as mono-, di- or polysaccharides such as glucose, fructose, mannose, xylose, galactose, ribose, sorbose, ribulose, lactose, maltose, sucrose, raffinose, starch or cellulose, complex sugar sources such as molasses, sugar phosphates such as fructose 1,6-bisphosphate, sugar alcohols such as mannitol, polyols such as glycerol, alcohols such as methanol or ethanol, carboxylic acids such as citric acid, lactic acid or acetic acid, fats such as soybean oil or rapeseed oil, amino acids such as an amino acid mixture, for example casamino acids (Difco) or single amino acids or aminosaccharides, and the latter may simultaneously be used as nitrogen source.

Advantageous nitrogen sources are organic or inorganic nitrogen compounds or materials containing these compounds. Examples are ammonium salts such as $NH_4Cl$ or $(NH_4)_2SO_4$, nitrates, urea, or complex nitrogen sources such as corn steep liquor, brewer's yeast autolysate, soybean meal, wheat gluten, yeast extract, meat extract, casein hydrolysate, yeast or potato protein, which may often also serve as carbon source.

Examples of inorganic salts are the salts of calcium, magnesium, sodium, cobalt, molybdenum, manganese, potassium, zinc, copper and iron. The chloride, sulfate and phosphate ion should be particularly mentioned as anion in these salts.

Further growth factors are added where appropriate to the nutrient medium, such as vitamins or growth promoters such as biotin, riboflavin, thiamine, folic acid, nicotinic acid, pantothenate or pyridoxine, amino acids such as alanine, cysteine, proline, aspartic acid, glutamine, serine, phenylalanine, ornithine or valine, carboxylic acids such as citric acid, formic acid, pimelic acid or lactic acid, or substances such as dithiothreitol.

The mixing ratio of said nutrients depends on the organism and on the type of fermentation and is established in the individual case. The medium components may all be present at the start of the fermentation after they have been sterilized separately or sterilized together if necessary, or else be added continuously or batchwise as required during the fermentation.

The cultivation conditions are established so that the organisms grow optimally and that the best possible yields are obtained. Preferred cultivation temperatures are 15° C. to 40° C. Temperatures between 25° C. and 37° C. are particularly advantageous. The pH is preferably maintained in a range from 3 to 9. pH values between 5 and 8 are particularly advantageous. In general, a sufficient incubation time is from a few hours up to some days, preferably from 8 hours up to 21 days, particularly preferably from 4 hours up to 14 days. The maximum amount of product accumulates in the medium during this time.

Advantageous ways of optimizing media can be found by the skilled worker in, for example, the textbook Applied Microbial Physiology, A Practical Approach (Eds. P. M. Rhodes, P. F. Stanbury, IRL-Press, 1997, pages 53–73, ISBN 0 19 963577 3). Advantageous media and cultivation conditions for Amycolatopsis are to be found in Nadkarni et al. (J. Antibiot, 1994, 334–341) on page 336 and 337, or DE 42 26 192, example 16+17 (pages 11 and 12), EP-A-0 468 504, example 1–4 (pages 4–6) and page 2 (lines 20–40) and EP-30 521 408, example 1. The compound to be halogenated can be added to the medium right at the start of the fermentation or continuously or batchwise during the fermentation. The conversion can be followed using conventional analytical methods, for example thin-layer chromatography, HPLC or GC.

The process according to the invention can be carried out continuously or batchwise in batch or fed-batch mode.

Depending on the organism, the pH can be controlled or not controlled during the fermentation. The fermentation is usually carried out at a pH between 5 and 9, preferably 6 and 9.

An analytical method for glycopeptide antibiotics is to be found, for example, in Nadkarni et al. (J. Antibiotics 1994: 334–341).

If the process according to the invention is carried out with free enzymes (crude extract or purified enzyme), it is possible and advantageous to operate in a wider temperature range. On the one hand, this temperature range is determined by the reaction rate, meaning that very low temperatures lead to a low reaction rate but, on the other hand, it is determined by the temperature stability of the enzyme, meaning that high temperatures lead to denaturation of the enzyme. For these reasons, a temperature range between 5 and 80° C., preferably from 10 to 60° C., particularly preferably from 20 to 40° C., is advantageous. Resting cells are also suitable for the process and can, where appropriate, just like the enzymes, advantageously be immobilized. For better conversion, the cell membranes are destabilized so that the precursors and the product can reach the reaction site (enzyme) more easily. The destabilization can take place, for example, with various alkali metal or alkaline earth metal salts such as lithium, rubidium or calcium salts or by treatment with solvents.

The halogenases or halogenase genes used in the process according to the invention belong to the NADH-dependent halogenases which differ from the haloperoxidases on the basis of their regio- and/or stereoselectivity.

In addition, they show a broad substrate specificity. They preferentially halogenate aromatic residues.

The preferred halogenase from Amycolatopsis mediterranei has 491 amino acids (SEQ ID NO:2). Its gene has been called bhaA. The enzyme has an NADH/FAD binding site. At the N terminus of the bhaA gene there is a sequence motif (β&β fold) which is presumably involved in the ADP binding of FAD- and NAD-dependent enzymes. An Asp residue which may make FAD binding possible is conserved in position 304 of the protein. bhaA may thus also possibly bind FAD. With growing cells it is not a problem to provide NADH or NAD$^+$which is necessary for the reaction, because this can take place from the metabolism of the growing organism. Nor does the provision of other necessary factors represent a problem.

If resting cells or enzyme preparations are used in the process according to the invention, it is advantageous to add other substances and cofactors to the reaction solution.

In the simplest case, with resting cells this is the addition of a carbon source, by which the reducing equivalents could be regenerated.

If the process according to the invention is carried out with free or immobilized enzymes, it is advantageous to add at least one natural or synthetic electron donor, such as NADH, methyl- or benzylviologen, to the reaction solution.

These electron donors are advantageously either added continuously to the reaction solution or else regenerated in a further reaction. This can take place, for example, in an electrochemical or enzymatic reaction. Regeneration reactions of these types are described, for example, in EP-B-0 023 346, DE 29 30 087 C2, DE 33 07 094 A1 or DE 36 31 228 A1.

Thus, DE 29 30 087 C2 describes, for example, the regeneration of NADH from NAD using formate dehydrogenase in the presence of formate. The molecular weight of the NAD$^+$/NADH was advantageously increased using polyethylene glycol so that it can be retained in a membrane reactor and thus is permanently available for the reaction (see DE 29 30 087 C2, columns 1 and 2). The same is described in EP-B-0 023 346 and DE 33 07 094 A1.

DE 36 31 228 describes the regeneration of NAD$^+$with viologens (CAV and CYV). Another advantageous embodiment is coexpression of a cofactor-regenerating enzyme, for example of formate dehydrogenase with the halogenase, or cocultivation with organisms which make regeneration possible.

The abovementioned publications on regeneration are incorporated herein by reference.

The process according to the invention is advantageously carried out in the presence of a buffer or under pH-controlled conditions in the case where free or immobilized enzymes are used.

The process is carried out at a pH between 4 and 10, preferably between 5 and 9, particularly preferably between 6 and 9.

It is advantageous to add $C_1$–$C_8$-mono- or dicarboxylic acids such as acetic acid, propionic acid or citric acid to the reaction solution. These can be used at the same time to produce the reaction buffer.

The invention further relates to a nucleic acid fragment comprising a halogenase which is (a) encoded by the sequence specified in SEQ ID NO:1 or a sequence derived therefrom on the basis of the degeneracy of the genetic code, or is (b) encoded by a nucleic acid sequence which codes for a functional fragment of (a) or (c) by a sequence which hybridizes with (a) or (b) under standard conditions, or is (d) encoded by a sequence which has more than 30% identity or more than 60% similarity with the sequence specified under (a), and which is functionally linked to one or more homologous or heterologous regulatory signals to increase gene expression and/or protein expression, and/or whose natural regulation is switched off.

The nucleic acid fragment according to the invention means said halogenase sequences or their functional equivalents which advantageously are functionally linked to one or more regulatory signals to increase gene expression. These regulatory sequences are, for example, sequences to which inducers or repressors bind and thus control expression of the nucleic acid. In addition to these novel regulatory sequences or in place of these sequences it is possible for the natural regulation of these sequences to be present in front of the actual structural genes and, where appropriate, to have been genetically modified so that the natural regulation has been switched off and the expression of the genes has been increased. However, the gene construct can also, in a less preferred form, have simpler structure, that is to say no additional regulatory signals have been inserted in front of the sequence SEQ ID NO:1 or its functional equivalents (see page 32 a to d) and the natural promoter with its regulation has not been deleted. Instead, the natural regulatory sequence has been mutated so that regulation no longer takes place, and gene expression is increased. These modified promoters can also be placed on their own in front of the natural genes to increase the activity. The gene construct may in addition advantageously contain one or more enhancer sequences functionally linked to the promoter, which make increased expression of the nucleic acid sequence possible. It is also possible to insert additional advantageous sequences at the 3' end of the DNA sequences, such as further regulatory elements or terminators. One or more copies of the halogenase gene may be present in the gene construct.

Advantageous regulatory sequences for the process according to the invention are, for example, present in promoters such as cos, tac, trp, tet, trp-tet, lpp, lac, lpp-lac, lacI$^{q}$, T7, T5, T3, gal, trc, ara, SP6, $\lambda$-$P_R$ or in the $\lambda$-$P_L$ promoter, which are advantageously used in Gram-negative bacteria. Further advantageous regulatory sequences are present, for example, in the Gram-positive promoters amy and SPO2, in the yeast or fungal promoters ADC1, MF$\alpha$, AC, P-60, CYC1, GAPDH, TEF, rp28, ADH or in the plant promoters CaMV/35S [Franck et al., Cell 21(1980) 285–294], PRP1 [Ward et al., Plant. Mol. Biol.22(1993)], SSU, OCS, lib4, usp, STLS1, B33, LEB4, nos or in the ubiquitin or phaseolin promoter. Also advantageous in this connection are the promoters of pyruvate decarboxylase and of methanol oxidase from, for example, Hansenula. Examples of other advantageous plant promoters are a benzenesulfonamide-inducible (EP 388186), a tetracycline-inducible (Gatz et al., (1992) Plant J. 2,397–404), an abscisic acid-inducible (EP335528) and an ethanol- or cyclohexanone-inducible (WO9321334) promoter. Particularly advantageous plant promoters are those which ensure expression in tissues or plant parts in which the biosynthesis of purines and its precursors takes place. Particular mention should be made of promoters which ensure leaf-specific expression. Those to be mentioned are the promoter of cytosolic FBPase from potato or the ST-LSI promoter from potato (Stockhaus et al., EMBO J. 8 (1989) 2445–245). It is also possible and advantageous to use the promoter of phosphoribosyl-pyrophosphate amidotransferase from Glycine max (see also Genbank Accession Number U87999) or another node-specific promoter as in EP 249676.

It is possible in principle to use all natural promoters with their regulatory sequences like those mentioned above for the process according to the invention. It is additionally possible and advantageous to use synthetic promoters.

The nucleic acid fragment (=gene construct) may also, as described above, contain further genes which are to be introduced into the organisms. These genes may be under separate regulation or under the same regulatory region as the halogenase genes. These genes are, for example, further biosynthesis genes which make increased synthesis, for example of glycopeptide antibiotics, or the synthesis of novel hydride antibiotics, possible or cofactor-regenerating enzymes. The nucleic acid fragment preferably contains SEQ ID NO:1.

For expression, the nucleic acid fragment is inserted into the abovementioned host organism, advantageously in a vector such as a plasmid, a phage, or other DNA, which makes optimal expression of the genes possible in the host. Examples of suitable plasmids are in E. coli pLG338, pACYC184, pBR322, pUC18, pUC19, pKC30, pRep4, pHS1, pHS2,pPLc236, pMBL24, pLG200, pUR290, pIN-III$^{113}$-B1, $\lambda$gt11 or pBdCI, in Streptomyces pIJ101, pIJ364, pIJ702 or pIJ361, in Bacillus pUB110, pC194 or pBD214, in Corynebacterium pSA77 or pAJ667, in fungi pALS1, pIL2 or pBB116, in yeasts 2 $\mu$, pAG-1, YEp6, YEp13 or pEMBLYe23 or in plants pLGV23, pGHlac$^+$, pBIN19, pAK2004 or pDH51 or derivatives of the abovementioned plasmids. Said plasmids represent a small selection of the possible plasmids. Further plasmids are well known to the skilled worker and can be found, for example, in the book Cloning Vectors (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press), chapters 6/7, pp. 71–119.

The nucleic acid fragment advantageously contains, for expression of the other genes present, in addition 3' and/or 5' terminal regulatory sequences to increase the expression, which are selected for optimal expression according to the selected host organism and gene or genes.

These regulatory sequences are intended to make targeted expression of the genes and protein expression possible. This may mean, for example, depending on the host organism that the gene is expressed and/or overexpressed only after induction, or that it is immediately expressed and/or overexpressed.

The regulatory sequences or factors may moreover preferably have a beneficial effect on expression of the introduced genes and thus increase it. Thus, strengthening of the regulatory elements may advantageously take place at the level of transcription by using strong transcription signals such as promoters and/or enhancers. However, besides this, it is also possible to enhance translation by, for example, improving the stability of the mRNA.

The substrate specificity can be increased and/or altered in the desired direction by various mutagenesis methods, for example site-directed mutagenesis, error-prone PCR and/or gene shuffling.

It is also possible and advantageous to increase the enzyme activity. An increase in the enzyme activity or in the substrate specificity can be achieved, for example, by modifying the catalytic site. An increase can also be achieved by modifying the enzyme so that inhibitors of the enzyme no longer bind or now bind only very weakly.

Methods advantageous for modifying the enzyme are as mentioned above, for example site-directed mutagenesis (see D. M. Glover et al., DNA Cloning, Vol. 1, 1995, IRL Press, chapter 6, pages 193 et seq., ISBN 019-963476-9), random mutagenesis with PCR using dITP (Spee et al., Nucleic Acids Res., Vol. 21, No. 3, 1993: 777–778) or the in vitro recombination technique (Stemmer, Proc. Natl. Acad. Sci., USA, Vol. 91, 1994: 10747–10751).

In another embodiment of the vector, the gene construct according to the invention can also be inserted into the microorganisms advantageously in the form of a linear DNA and be integrated into the genome of the host organism by heterologous or homologous recombination. This linear DNA may consist of a linearized plasmid or only of the nucleic acid fragment as vector.

It is also possible to use as vector any plasmid (but in particular a plasmid which harbors the origin of replication of the 2 $\mu$ plasmid from S. cerevisiae) which undergoes autonomous replication in the cell, but also, as described above, a linear DNA fragment which integrates into the genome of the host. This integration can take place by heterologous or homologous recombination but, as mentioned, preferably by homologous recombination (Steiner et al., Genetics, Vol. 140, 1995: 973–987).

Further vectors suitable and advantageous for the genera Streptomyces, Rhodococcus, Nocardia or Amycolatopsis are described, for example, in Matsushima et al. (J. Bacteriol., Vol. 169, No. 5, 1987: 2298–2300, Table 1), de Schrijver et al. (Appl. Environ. Microbiol., Vol. 63, No. 5, 1997: 1911–1916, Table 1) or Bierman et al. (Gene 116, 1992: 43–49, Table 1).

For optimal expression of the heterologous helogenase genes in organisms it is advantageous to modify the nucleic acid sequences to be appropriate for the specific codon usage employed in the organism. The codon usage can easily be established by computer analyses of other, known genes in the relevant organism.

An increase in the expression of the halogenase genes can take place at various levels, such as by increasing the gene copy number or by enhancing gene expression by modifying the regulatory elements. Thus, strengthening of the regulatory elements can preferably take place at the level of transcription (e.g. use of stronger promoters and/or enhancers) or at the level of translation (e.g. increasing the stability of the mRNA). It is possible and advantageous to achieve complete cloning of the glycopeptide antibiotics by overexpression.

The invention further relates to the sequence specified in SEQ ID NO:1, and to the protein sequence derived therefrom (SEQ ID NO:2).

Overexpression is to be described herein by way of example for Amycolatopsis. The bhaA gene is cloned after amplification to produce suitable cleavage sites downstream of the strong erythromycin promoter (ermE). The latter functions well in Amycolatopsis. Further suitable promoters are the constitutive phage promoter SF 14 of phage 718 (Labes et al. Microbiology 147, 1997: 1503–1512) or the thiostrepton-inducible inducible tipA promoter (Murakami et al., 1989, J. Bacteriol. 171, 1459–66, Takano et al., 1995, Gene, 166: 133–137). Expression of the gene takes place with replicative vectors or by integrative vectors. Expression by integrative vectors, for example via the attachment site of the phage phiC31 (Muth, G., Brolle, G. F., Wohlleben, W., 1999), has a number of advantages; thus, there is no adverse effect on the preparation of products, e.g. antibiotics, and stabilization of genes by antibiotic addition to the medium is unnecessary. An advantageous plasmid for the integration is, for example, pSET152 (Bierman et al., 1992, Gene 116, 43–49). Advantageous replicative Amycolatopsis vectors which may be mentioned are pMEA100 (Moretti, P. et al., 1985, Plasmid, 14, 126–133), pMEA300 (Vrijbloed, J. W. et al., 1995, Plasmid, 34, 96–104) or pA387 (Lal, R. et al., 1991, Appl. Environ. Microbiol. 57, 665–67) and derivatives thereof.

Expression is also possible and advantageous with the melC promoter (Schmitt John, T. and Engels, J. W., 1992, Appl. Microbiol. Biotechnol. 36, 493–498), for example with the plasmid pIJ702 (Katz, E. et al., 1982, J. Gen. Microbiol., 192, 2703–2714) or downstream of the ermE promoter (Bibb, M. J. and Janssen, G. R. Unusual features of transcription and translation of antibiotic resistance genes in antibiotic producing Streptomyces, In Proceedings of the fifth International Symposium on the genetics of Industrial Microorganismus, pp. 309–318, Edited by M. Alacevic, D. Hranneli and Z. Toman, Karlovac, Yugoslavia: Ojnejin Prica Printing Works) with plasmid pM4 (Quiros, L. M. et al., 1998, Mol. Microbiol., 28, 1177–1185).

The invention also includes organisms which comprise SEQ ID NO:1 or the nucleic acid fragment described above or the vector described.

EXAMPLES

Example 1

Identification and Isolation of the Balhimycin Halogenase Gene bhaA

The Balhimycin biosynthesis gene cluster was identified and cloned using a reverse genetics approach. The conserved primers Gly1 and Gly7 were derived from glycosyl transferases (GtfA–GtfE) whose genes were isolated from the glycopeptide antibiotic-producers A. orientalis A82846 and A. orientalis C329.4 and which are involved in the biosynthesis of the glycopeptide antibiotics chloroeremomycin (A82846B) and vancomycin (Solenberg et al., 1997) [sequence of primer Gly1: 5'-TCCCCCCGGGIWSSCGCGGIGACGTSGA-3'; sequence of primer Gly7: 5'-TCCCCCCGGGTGGTGGATSRCSGCSGCSACSCGI CCGAA-3' (I: inosine; S: C/G; W: A/T)]. It was possible with the aid of PCR (see below) to amplify an internal glycosyltransferase gene fragment about 900 bp in size ('bgtfB') from the chromosome of the balhimycin producer A. mediterranei DSM5908.

PCR:

PCR apparatus: RoboCycler Gradient 40 Thermocycler (Stratagene)

Kit: Expand High Fidelity PCR System (Boehringer)

PCR mixture (100 µl):
  50 pmol of primer Gly1
  50 pmol of primer Gly7
  0.1 µg of genomic DNA from A. mediterranei DSM5908
  200 µM dNTPs (each)
  10 µl of 10 X reaction buffer
  1.5 µM of $MgCl_2$
  3 µl of MSO
  3,5 U of Taq DNA polymerase PCR program:

Denaturation: 95° 5 min

Polymerase addition: 72° 10 min

Denaturation: 94° 70 sec

Annealing: 59–63° 70 sec

Elongation: 72° 90 sec 35 cycles

Elongation: 72° 10 min

This fragment was employed, after construction of a cosmid gene bank from A. mediterranei in the cosmid vector pOJ446 (construction of the gene bank as in Gaisser, S. et al., 1997, J. Bacteriol. 179: 6271–6278) in Southern hybridization experiments (Sambrook, J., Fritsch, E. F. and Maniatis, T. (1989). Molecular Cloning: a Laboratory Manual, 2nd edn. Cold Spring Harbor, N.Y.: Cold Spring Harbor Laboratory) to identify the putative balhimycin biosynthesis gene cluster. It was possible in this way to identify the cosmid 16.1 with an insert of about 36 kb. It was found in sequence analyses that the region homologous to the gene probe codes for a total of three glycosyltransferase genes (bgtfA–bgtfC), the products derived from which genes show very great similarity with glycosyltransferases (GtfA–GtfC) previously isolated from other glycopeptide antibiotic producers (Solenberg et al. 1997, see above).

It was possible to show unambiguously by various gene inactivation experiments that various genes in the cluster on 16.1, such as genes for glycosyltransferases and cytochrome P450-dependent monooxygenases, are involved in balhimycin biosynthesis. This provided proof of the identification of the balhimycin biosynthesis gene cluster.

The experiments were carried out as described in Pelzer et al. (Antimicrob. Agents Chemother. July 1999, Vol 43, No. 7, in press und J. Biotechnol., 56, 1977, 115–128).

After identification of the halogenase gene bhaA (see example 2) it was found that bhaA is flanked by three oxygenase genes (oxyA–C) and the three glycosyltransferase genes (bgtfA–C). It was possible to localize the gene to a BamHI fragment which is about 3 kb in size and had previously been subcloned into the vector pVC19.

Double-stranded sequencing (Sanger, F. S. et al., 1977, Proc. Natl. Acad. Sci, USA, 74: 5463–5467) of the fragment revealed a size of 3088 bp with an average G/C content of 68.8%. ORF analysis (Staden, R., and Mc Lachlan, A. D., 1982, Nucleic Acids Res., 10: 141–156) of the nucleotide sequence led to the identification of three open reading frames (see FIG. 1). The gene bhaA is located on the fragment flanked by part of the oxygenase gene oxyC and part of the glycosyltransferase gene bgtfA. The gene has an ATG start codon and a TGA stop codon. It was not possible to find a Streptomyces—typical promoter in this sequence. The potential RBS (=ribosome binding site) AGAGG is located 11 nucleotides in front of the start codon.

Example 2

Demonstration of the Function of the bhaA Gene

The function of the bhaA gene was demonstrated by producing an in-frame deletion mutant. The in-frame deletion was produced in order to preclude any polar effect on following genes from foreign DNA, which are frequently observed in gene disruption or gene replacement experiments. The in-frame deletion mutant was produced in 2 steps.

Firstly, the gene replacement mutant PH3 was produced and was used exclusively for preparing the in-frame deletion mutant PH4. The starting plasmid for constructing the necessary vectors was a pVC18 derivative (pVC18B3.0) which harbors the BamHI fragment which is 3088 bp in size and on which is located, inter alia, the bhaA gene. All DNA isolations, restriction cleavages and clonings were carried out, unless described otherwise, as described in Sambrook, J., Fritsch, E. F. and Maniatis, F., 1989, Molecular Cloning: a Laboratory Manual, 2nd edn. Cold Spring Harbor, N.Y.: Cold Spring Harbor Laboratory.

This plasmid was linearized by an MluI digestion. The cleavage site is unique and is located approximately in the middle of the fragment. Introduction of a 969 bp in-frame deletion in the bhaA gene then took place with the aid of a PCR. Two primers (primers 2 and 3) were designed for this in such a way that, firstly, the in-frame deletion was introduced and, additionally, a unique BglII cleavage site was produced by the primers.

The primers had the following sequence:

Primer 2: 5'-CTCACAGATCTGATACCGCGGGAAA-3'
Primer 3: 5'-CTACCAGATCTACGTGAACGAGGAG-3'
PCR apparatus: Thermocycler PTC100 von MJ Research
Kit: Expand High Fidelity PCR System (Boehringer)
PCR mixture (50 µl):
Master-Mix 1 (25 µl):
  200 µM dNTP mix
  200 nM primer 2
  200 nM primer 3
  1–10 ng of template DNA
  1.5 µl of DMSO
Master-Mix 2 (25 µl):
  5 µl of 10 X PCR buffer 2
  0.75 µl of enzyme mix
Pipette Master-Mix 1 and 2 together
PCR program:
Denaturation: 94° 3 min
Annealing: 65° 30 sec
Elongation: 68° 4 min
Denaturation: 95° 45 sec
10 cycles
Annealing: 65° 30 sec
Elongation: 68° 4 min+20 sec per cycle
Denaturation: 94°45 sec
15 cycles
Elongation: 72° 7 min The PCR fragment was religated to produce the vector pUC18BΔ. At the same time, to produce the gene replacement mutant PH3 the chloramphenicol resistance gene cat (Gil et al., 1985, Gene 38, 1–8) was inserted as BclI fragment into the BglII cleavage site. This vector was called pUC8cat. For insertion into A. mediterranei DSM5908, the two inserts were cloned as EcoRI/SphI fragment into the vector pSP1 (Pelzer et al., 1997) which is non-replicative in the balhimycin producer and can be employed for gene inactivation, to result in the plasmids pPH4 (deletion construct) and pPH3 (gene replacement construct).

Firstly the gene replacement mutant PH3 was produced. This was done by transforming the balhimycin producer with the plasmid pPH3 by means of direct transformation (Pelzer et al., 1997). It was possible by suitable selection (chloramphenicol resistance and erythromycin sensitivity, to identify the gene replacement mutant PH3 and verify it by Southern hybridizations (Sambrook, see above).

This gene replacement mutant PH3 was then transformed with the deletion plasmid pPH4. Initial selection was for integration of the complete vector by homologous recombination (chloramphenicol resistance and erythromycin resistance. The selection pressure for vector elimination by homologous recombination was then removed. Chloramphenicol-sensitive and erythromycin-sensitive colonies were found in this way. It was possible by Southern hybridizations to verify the mutant PH4 as a correct in-frame deletion mutant in the bhaA gene.

HPLC/MS investigations and analysis of the isotope pattern revealed that PH4 now produced only unchlorinated balhimycin derivatives. This means that it was possible to show that BhaA is responsible for both chlorinations at AA position 2 and 6 (see following examples).

Example 3

Biosynthesis Metabolites of the Mutant PH4 a) Results of the analysis by electrospray mass spectrometry Mutant pH4

The product spectrum from the clone pH4 corresponded to that of the wild type, apart from the lack of chlorination. However, unglycosylated compounds (comp. $7^\Delta$, $8^\Delta$, $9^\Delta$) were detected in the culture filtrates from this mutant but were not detected in the product spectrum from the wild type.

TABLE 1

Product spectrum of the compounds identified by HPLC/ES-MS of the wild type and the mutants. The unchlorinated biosynthesis products are indicated by "Δ".

| Code | Metabolite | M.W. | Wt | PH4 |
|---|---|---|---|---|
| (1) | Balhimycin | 1445.4 | + | |
| (1$^\Delta$) | Dechlorobalhimycin | 1377.5 | | + |
| (2) | Balhimycin V | 1586.5 | + (1604, 5) | |
| (2$^\Delta$) | | 1518.6 | | ○ (1536, 4) |
| (3) | Methylbalhimycin | 1459.4 | + | |
| (3$^\Delta$) | | 1391.5 | | + |
| (5) | M43C | 1318.4 | + | |
| (5$^\Delta$) | | 1250.4 | | + |
| (6) | Devancosaminovancomycin | 1304.3 | + | |
| (6$^\Delta$) | | 1236.4 | | + |
| (7) | Methyl aglycone | 1156.3 | | |

TABLE 1-continued

Product spectrum of the compounds identified by
HPLC/ES-MS of the wild type and the mutants. The
unchlorinated biosynthesis products are indicated by "Δ".

| Code | Metabolite | M.W. | Wt | PH4 |
|---|---|---|---|---|
| (7$^\Delta$) | | 1088.4 | | + |
| (8) | HD-1142 | 1142.3 | | |
| (8$^\Delta$) | | 1074.4 | | + |
| (9) | HD-1128 | 1128.3 | | |
| (9$^\Delta$) | | 1060.4 | | + |

"Δ" = high ion intensities; "+" = moderate ion intensities; "○" = low ion intensities The results of the investigation of the culture filtrates by HPLC/MS showed that the chlorination no longer takes place owing to the in-frame mutation. Detection by mass spectrometry via the characteristic isotope distributions is chemically unambiguous. All the compounds detected from the mutant PH4 showed a mass difference of 68 amu=2 Cl atoms from the compounds detected with the wild type.

The MS analyses allowed only qualitative, or at the most semiquantitative, conclusions to be drawn about the amount of the individual metabolites produced. Nevertheless, a certain trend in the quantity of the biosynthesis products was detectable from the intensities of the molecular ions.

Upon analyzing the ES mass spectra of dechlorobalhimycin (mutant PH4) and balhimycin (wild type), the characteristic isotope patterns prove inactivation of the halogenase BhaA. Line spectra correspond to the theoretically expected isotope distributions.

b) Optimized purification

Prepurification of the peptides

To remove the erythromycin employed for selection, the filtered culture supernatants were each extracted three times with an equal volume of ethyl acetate. Before loading onto the XAD16 column, the culture supernatants were filtered once more through a porcelain frit (filter G3) and eluted with the stepped gradients indicated in Table 2. The fractions were investigated by HPLC/MS for the content of crude peptide and, after removal of the solvent in vacuo, freeze dried.

TABLE 2

Parameters for the chromatographic separation on XAD adsorber resin

| Parameter | Dechloro metabolites |
|---|---|
| Column | XAD-16 |
| Bed volume | 500 ml |
| Equilibration buffer | $H_2O$ |
| Sample | 400 ml in Medium |
| Eluent (stepped gradient) | Water/methanol (1 1 of eluent per step) |
| I | 0% methanol |
| II | 10% methanol |
| III | 20% methanol |
| IV | 40% methanol |
| V | 60% methanol |
| VI | 80% methanol |
| VII | 100% methanol |
| Number of fractions: | 7 |
| Flow rate | 4 bed volumes/h |

Preparative RP 18 HPLC

The crude peptide fractions were dissolved in the initial gradient ($H_2O$: ACN (9:1); 0,1% TFA) and filtered (Millex®-GV; 0,22 μm; Millipore). The fractions collected after the separation were analyzed by ES-MS, freeze-dried and combined.

Analytical parameters

Chromatograph Waters 600 Multisolvent Delivery System (Waters)

Detector Lamda-Max, Model 481 (Waters)

Column Nucleosil RP-C18, 5 μm, 20×250 mm (Grom, Herrenberg)

Sample loading valve Altex 210 Valve (Beckmann)

Amount loaded 10 mg of crude peptide

Separation parameters

Eluents A: water (0.1% TFA) B: acetonitrile (0.1% TFA)

Flow rate 10 ml/min

Detection wavelength 214 nm

TABLE 3

Gradient for separating the dechloro metabolites
HD metabolites

| t/min | % A | % B |
|---|---|---|
| 0 | 90 | 10 |
| 12 | 80 | 20 |
| 41 | 80 | 20 |
| 42 | 78 | 22 |
| 47 | 76 | 24 |
| 57 | 74 | 26 |
| 62 | 70 | 30 |
| 67 | 68 | 32 |
| 90 | 100 | 0 | c) Electrospray mass spectrometry

The ES mass spectra were recorded on an API-III triple quadrupole mass spectrometer (Sciex, Thornhill, Canada). Unless noted otherwise, the samples were dissolves in ACN/$H_2O$ (1:1, 0.1% formic acid), and the spectra were recorded in positive ion mode. The sample was fed in by a microbore pump (140A Solvent Delivery System, ABI, Weiterstadt) at a flow rate after split of 5 μl/min. A UV detector (Linear UVVIS 204, Linear Instruments, Reno, Nev.) was used for detection. The mobile phase used was 0.1% trifluoroacetic acid (eluent A) and acetonitrile with 0.1% trifluoroacetic acid (eluent B). The separations took place on an analytical column (Nucleosil RP-C18, 5 μm, 2×100 mm, Grom, Herrenberg).

Dechlorobalhimycin

An optimal gradient was used to detect the dechlorobalhimycin metabolites (Table 4).

TABLE 4

Optimized gradient for the HPLC/NS analysis of dechlorobalhimycin derivatives

| t (min) | 0 | 1 | 15 | 17 |
|---|---|---|---|---|
| $H_2O$ | 95 | 83 | 80 | 0 |
| ACN | 5 | 17 | 20 | 100 |

We claim:

1. An isolated nucleic acid sequence comprising a nucleotide sequence which encodes a polypeptide having a halogenase activity selected from the group consisting of
   a) a nucleic acid sequence depicted in SEQ ID NO:1,
   b) a sequence derived from SEQ ID NO:1 on the basis of the degeneracy of the genetic code,
   c) a nucleic acid sequence which codes for a functional fragment of (a), and
   d) a sequence which has more than 95% identity or more than 97% similarity with the sequence specified under (a), and
      which is functionally linked to one or more homologous or heterologous regulatory signals to increase gene expression and/or protein expression, and/or whose natural regulation is switched off.

2. A vector comprising a nucleic acid fragment as claimed in claim 1.

3. A microorganism comprising a nucleic acid fragment as claimed in claim 1.

4. A nucleic acid sequence which encodes a polypeptide having halogenase activity selected from the group consisting of
   a) the sequence specified in SEQ ID NO:1,
   b) a sequence derived from SEQ ID NO:1 on the basis of the degeneracy of the genetic code,
   c) a nucleic acid sequence which codes for a functional fragment of (a), and
   d) a sequence which has more than 95% identity or more than 97% similarity with the sequence specified under (a).

5. An organism comprising a vector as claimed in claim 2.

* * * * *